United States Patent
Reyes et al.

(10) Patent No.: US 12,165,330 B2
(45) Date of Patent: Dec. 10, 2024

(54) LABELING, VISUALIZATION, AND VOLUMETRIC QUANTIFICATION OF HIGH-GRADE BRAIN GLIOMA FROM MRI IMAGES

(71) Applicants: Neosoma, Inc., Groton, MA (US); The University of Bern, Bern (CH)

(72) Inventors: Mauricio Reyes, Bern (CH); Michael Müller, Bern (CH); Aly Abayazeed, Northborough, MA (US)

(73) Assignees: Neosoma, Inc., Groton, MA (US); The University of Bern, Bern (CH)

( * ) Notice: Subject to any disclaimer, the term of this patent is extended or adjusted under 35 U.S.C. 154(b) by 0 days.

(21) Appl. No.: 17/992,546

(22) Filed: Nov. 22, 2022

(65) Prior Publication Data

US 2023/0083261 A1    Mar. 16, 2023

Related U.S. Application Data

(63) Continuation of application No. 17/733,579, filed on Apr. 29, 2022, now Pat. No. 11,526,994.
(Continued)

(51) Int. Cl.
*G06T 7/174* (2017.01)
*A61B 5/00* (2006.01)
(Continued)

(52) U.S. Cl.
CPC ............ *G06T 7/174* (2017.01); *A61B 5/0042* (2013.01); *G01R 33/5601* (2013.01);
(Continued)

(58) Field of Classification Search
None
See application file for complete search history.

(56) References Cited

U.S. PATENT DOCUMENTS 6,430,430 B1     8/2002 Gosche
11,207,324 B2 *  12/2021 Peterson .......... A61K 39/39558
(Continued)

OTHER PUBLICATIONS

Fukuoka et al., "Comparison of the added value of contrast-enhanced 30 fluid-attenuated inversion recovery and magnetization-prepared rapid acquisition of gradient echo sequences in relation to conventional postcontrast T1-weighted images for the evaluation of leptomeningeal diseases at 3T", American Journal of Neuroradiology 31(5): 868-873 (2010).
(Continued)

*Primary Examiner* — Nancy Bitar
(74) *Attorney, Agent, or Firm* — Erik A. Huestis; Lee Chedister; Foley Hoag LLP

(57) ABSTRACT

Systems, methods, and computer program products are provided for segmenting a brain tumor from various MRI sequencing techniques. A plurality of MRI sequences of a head of a patient are received. Each MRI sequence includes a T1-weighted with contrast image, a Fluid Attenuated Inversion Recovery (FLAIR) image, a T1-weighted image, and a T2-weighted image. Each image of the plurality of MRI sequences is registered to an anatomical atlas. A plurality of modified MRI sequences are generated by removing a skull from each image in the plurality of MRI sequences. A tumor segmentation map is determined by segmenting a tumor within a brain in each image in the plurality of modified MRI sequences. The tumor segmentation map is applied to each of the plurality of MRI sequences to thereby generate a plurality of labelled MRI sequences.

21 Claims, 17 Drawing Sheets

Related U.S. Application Data

(60) Provisional application No. 63/242,907, filed on Sep. 10, 2021.

(51) Int. Cl.
    *G01R 33/56*     (2006.01)
    *G06T 3/4046*     (2024.01)
    *G06T 7/00*     (2017.01)
    *G06T 7/38*     (2017.01)
    *G06T 7/62*     (2017.01)
    *G06V 10/32*     (2022.01)
    *G06V 10/764*     (2022.01)
    *G06V 10/82*     (2022.01)
    *G06T 3/40*     (2024.01)

(52) U.S. Cl.
    CPC ..... *G01R 33/5602* (2013.01); *G01R 33/5607* (2013.01); *G01R 33/5608* (2013.01); *G06T 3/4046* (2013.01); *G06T 7/0012* (2013.01); *G06T 7/38* (2017.01); *G06T 7/62* (2017.01); *G06V 10/32* (2022.01); *G06V 10/764* (2022.01); *G06V 10/82* (2022.01); *G06T 2207/10016* (2013.01); *G06T 2207/10088* (2013.01); *G06T 2207/20081* (2013.01); *G06T 2207/20084* (2013.01); *G06T 2207/30016* (2013.01); *G06T 2207/30096* (2013.01); *G06V 2201/03* (2022.01)

(56) References Cited

U.S. PATENT DOCUMENTS

| | | |
|---|---|---|
| 11,526,994 B1 | 12/2022 | Reyes et al. |
| 2009/0129649 A1* | 5/2009 | Djeridane .............. A61B 6/481 |
| | | 382/131 |
| 2012/0046539 A1 | 2/2012 | Visser |
| 2013/0131507 A1* | 5/2013 | Salazar-Ferrer ..... A61B 6/5217 |
| | | 600/431 |
| 2013/0182931 A1 | 7/2013 | Fan et al. |
| 2016/0110904 A1 | 4/2016 | Jeon et al. |
| 2017/0147908 A1* | 5/2017 | Chen ................... G06F 18/2415 |
| 2020/0275857 A1* | 9/2020 | Lou ........................ G01R 33/46 |
| 2021/0128710 A1* | 5/2021 | Bredlau ............. C07K 16/2818 |

OTHER PUBLICATIONS

International Search Report and Written Opinion for International Application No. PCT/US2022/043058 dated Feb. 2, 2023.

* cited by examiner

LABELING, VISUALIZATION, AND VOLUMETRIC QUANTIFICATION OF HIGH-GRADE BRAIN GLIOMA FROM MRI IMAGES

CROSS-REFERENCE TO RELATED APPLICATIONS

This application is a continuation of and claims priority to U.S. Non-provisional patent application Ser. No. 17/733,579, filed on Apr. 29, 2022, which claims the benefit of priority to U.S. Provisional Application No. 63/242,907, filed Sep. 10, 2021. The disclosures of the prior applications are considered part of the disclosure of this application, and are incorporated in their entirety into this application.

TECHNICAL FIELD

Embodiments of the disclosure generally relate to the field of medical diagnostics. In particular, embodiments of the disclosure relate to systems, methods, and computer program products for accurate segmentation and approximation of a tumor (e.g., brain tumor) in MRI imaging.

BACKGROUND

Gliomas are classified as Grades I to IV based on histology and clinical criteria. Grade I tumors are generally benign. Adult Grade II tumors are low-grade gliomas (LGGs) and include astrocytomas and oligodendrogliomas. Essentially, all Grade II lesions eventually progress to high-grade glioma (HGG) (Grade III/IV). High-grade gliomas are diffusely infiltrating tumors. To study tumor growth dynamics, surgical results, and tumor response after oncological treatment, the accurate assessment of tumor volume on brain MRIs is crucial. By convention, tumor appearance on contrast enhanced T1-weighted magnetic resonance images (MRIs) defines the tumor volume in quantitative studies, but methods of assessment vary much between studies. Additionally, the importance of measuring the non-enhancing component of the tumor is now recognized.

High-grade glioma tumors on brain MRIs may consist of two or more sub-components and these sub-components may be defined based on known clinical standard of differences in MRI signal intensities on 4 distinct MRI sequences (T1 weighted pre-contrast, T1 weighted post-contrast, T2 weighted and FLAIR) that are routinely acquired as part of everyday clinical practice.

Manual volume segmentation remains the gold standard for volume measurement. However, this is very time-consuming (45-60 minutes per MRI on average) and suffers from significant inter-rater and intra-rater variabilities. Tumor volumes are important to inform disease status during treatment through the Modified Response Assessment in Neuro-oncology (e.g., using the RANO criteria).

RANO (Response Assessment in NeuroOncology) is the international standard to determine tumor response to treatment. Using RANO improves median progression free survival (PFS) and objective response rates (ORRs). 3-D volumetric analysis is proven to be superior to the current 2-D method. Routine manual 2D analysis of brain tumors is very complicated, time consuming and inadequate for evaluating tumors, especially tumors with complex geometric shapes. Due to these limitations, RANO is not routinely followed. Current manual technique involves determining sum of the products of diameters (SPD) from one MRI slice instead of volume, which is analogous to measuring an iceberg by its tip. FIG. 1 shows an example where manual tumor volume annotation (i.e., white perpendicular crossing lines) missed a large portion of the adjacent tumor volume.

Accordingly, there is a need for improved methods and systems for semi-automatic and automatic segmentation to save time and resources in making volumetric measurements of different compartments of tumors (e.g., high-grade brain glioma).

BRIEF SUMMARY

Systems, methods, and computer program products are provided for segmenting a brain tumor from various MRI sequencing techniques. In various embodiments, a method is provided where a plurality of MRI sequences of a head of a patient are received. Each MRI sequence includes a T1-weighted with contrast image, a Fluid Attenuated Inversion Recovery (FLAIR) image, a T1-weighted image, and a T2-weighted image. Each image of the plurality of MRI sequences is registered to an anatomical atlas. A plurality of modified MRI sequences are generated by removing a skull from each image in the plurality of MRI sequences. A tumor segmentation map is determined by segmenting a tumor within a brain in each image in the plurality of modified MRI sequences. The tumor segmentation map is applied to each of the plurality of MRI sequences to thereby generate a plurality of labelled MRI sequences.

In various embodiments, a system includes a medical image database and a computing node including a computer readable storage medium having program instructions embodied therewith. The program instructions are executable by a processor of the computing node to cause the processor to perform a method where a plurality of MRI sequences of a head of a patient are received. Each MRI sequence includes a T1-weighted with contrast image, a Fluid Attenuated Inversion Recovery (FLAIR) image, a T1-weighted image, and a T2-weighted image. Each image of the plurality of MRI sequences is registered to an anatomical atlas. A plurality of modified MRI sequences are generated by removing a skull from each image in the plurality of MRI sequences. A tumor segmentation map is determined by segmenting a tumor within a brain in each image in the plurality of modified MRI sequences. The tumor segmentation map is applied to each of the plurality of MRI sequences to thereby generate a plurality of labelled MRI sequences.

In various embodiments, a computer program product includes a computer readable storage medium having program instructions embodied therewith. The program instructions are executable by a processor to cause the processor to perform a method where a plurality of MRI sequences of a head of a patient are received. Each MRI sequence includes a T1-weighted with contrast image, a Fluid Attenuated Inversion Recovery (FLAIR) image, a T1-weighted image, and a T2-weighted image. Each image of the plurality of MRI sequences is registered to an anatomical atlas. A plurality of modified MRI sequences are generated by removing a skull from each image in the plurality of MRI sequences. A tumor segmentation map is determined by segmenting a tumor within a brain in each image in the plurality of modified MRI sequences. The tumor segmentation map is applied to each of the plurality of MRI sequences to thereby generate a plurality of labelled MRI sequences.

DETAILED DESCRIPTION

Figure 1:
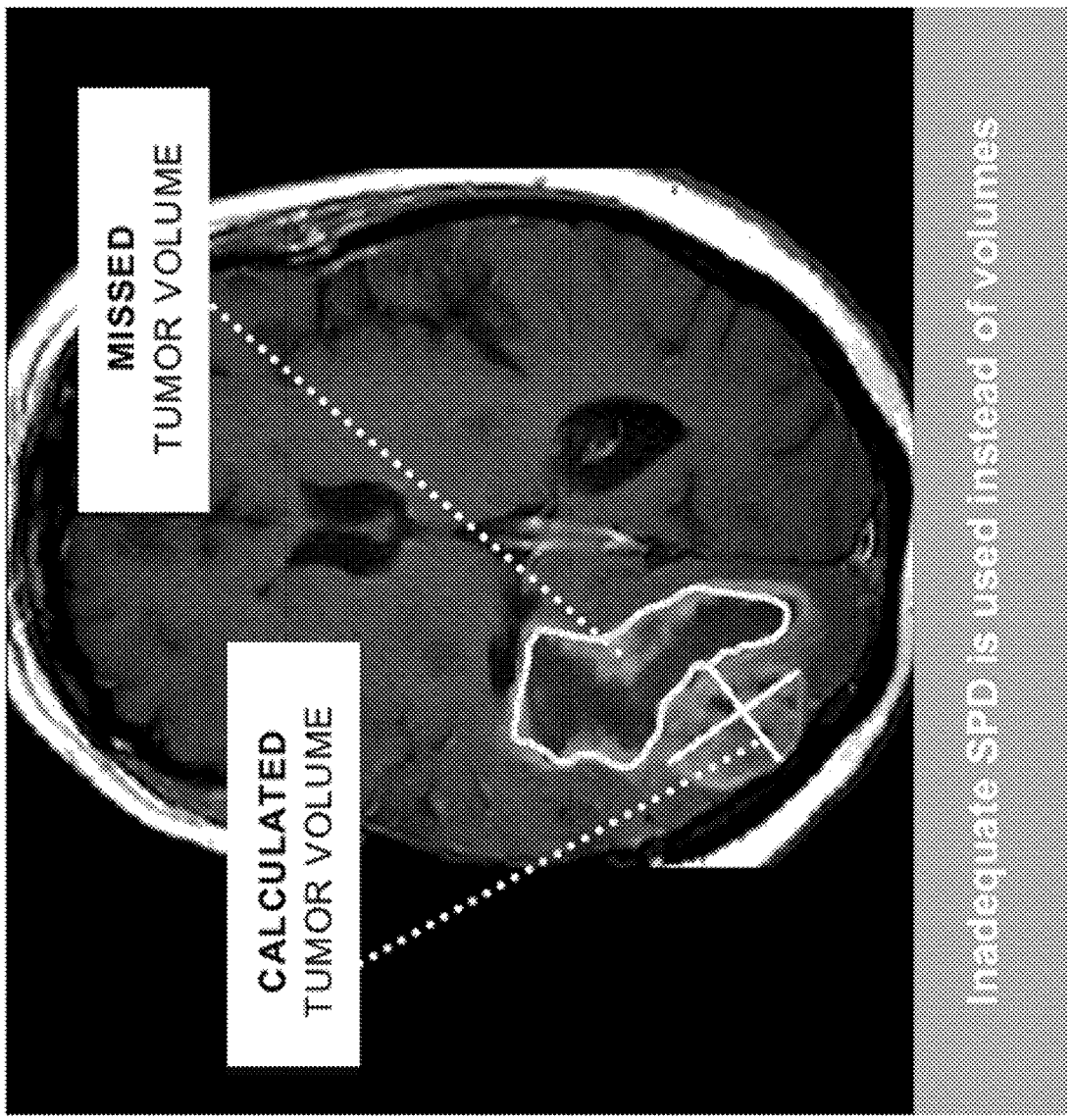
FIG. 1 illustrates an example where a manual segmentation missed a tumor volume.
Figure 2A:
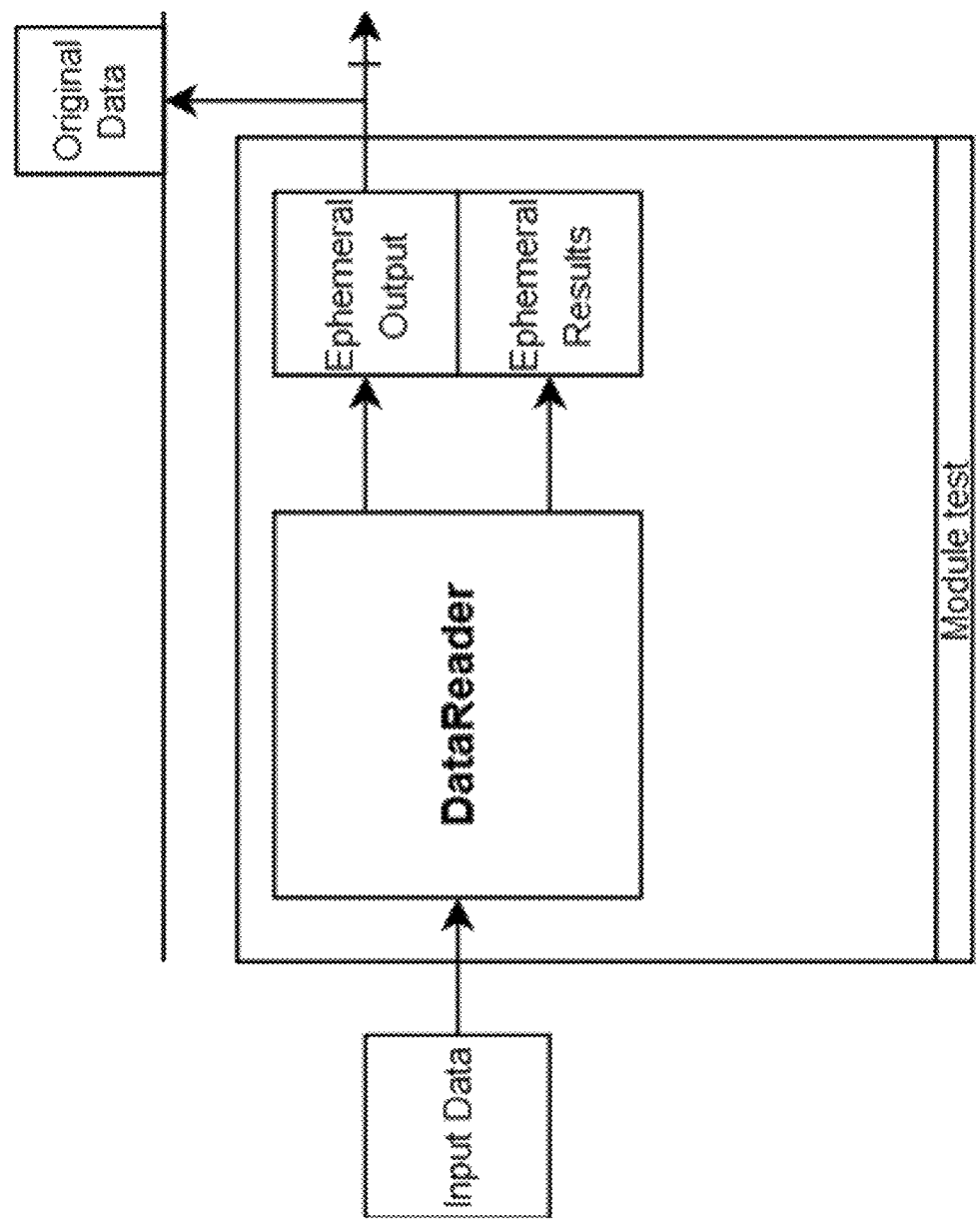
FIGS. 2A-2D illustrate an exemplary segmentation data pipeline according to embodiments of the present disclosure.
Figure 2B:
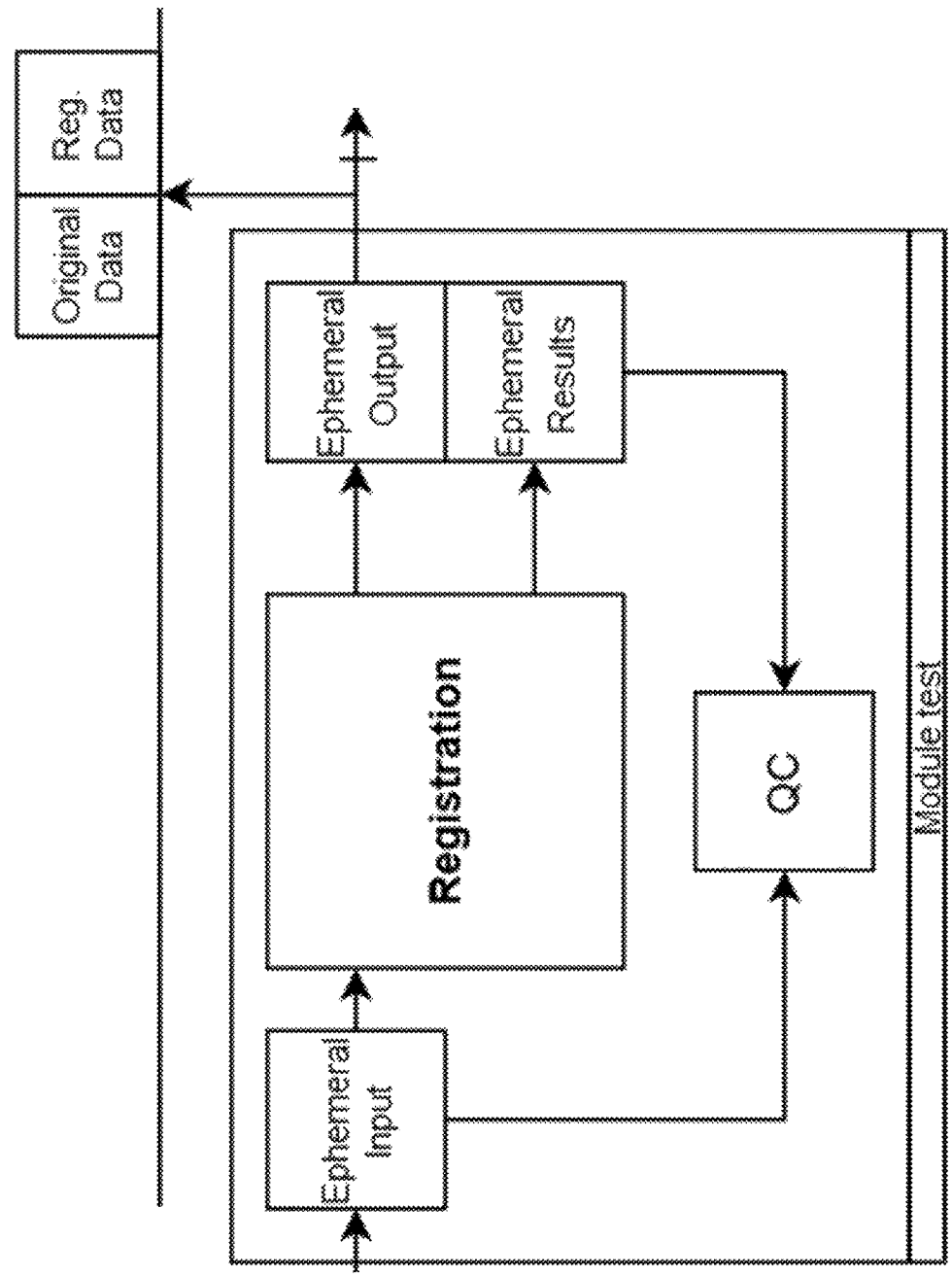
Figure 2C:
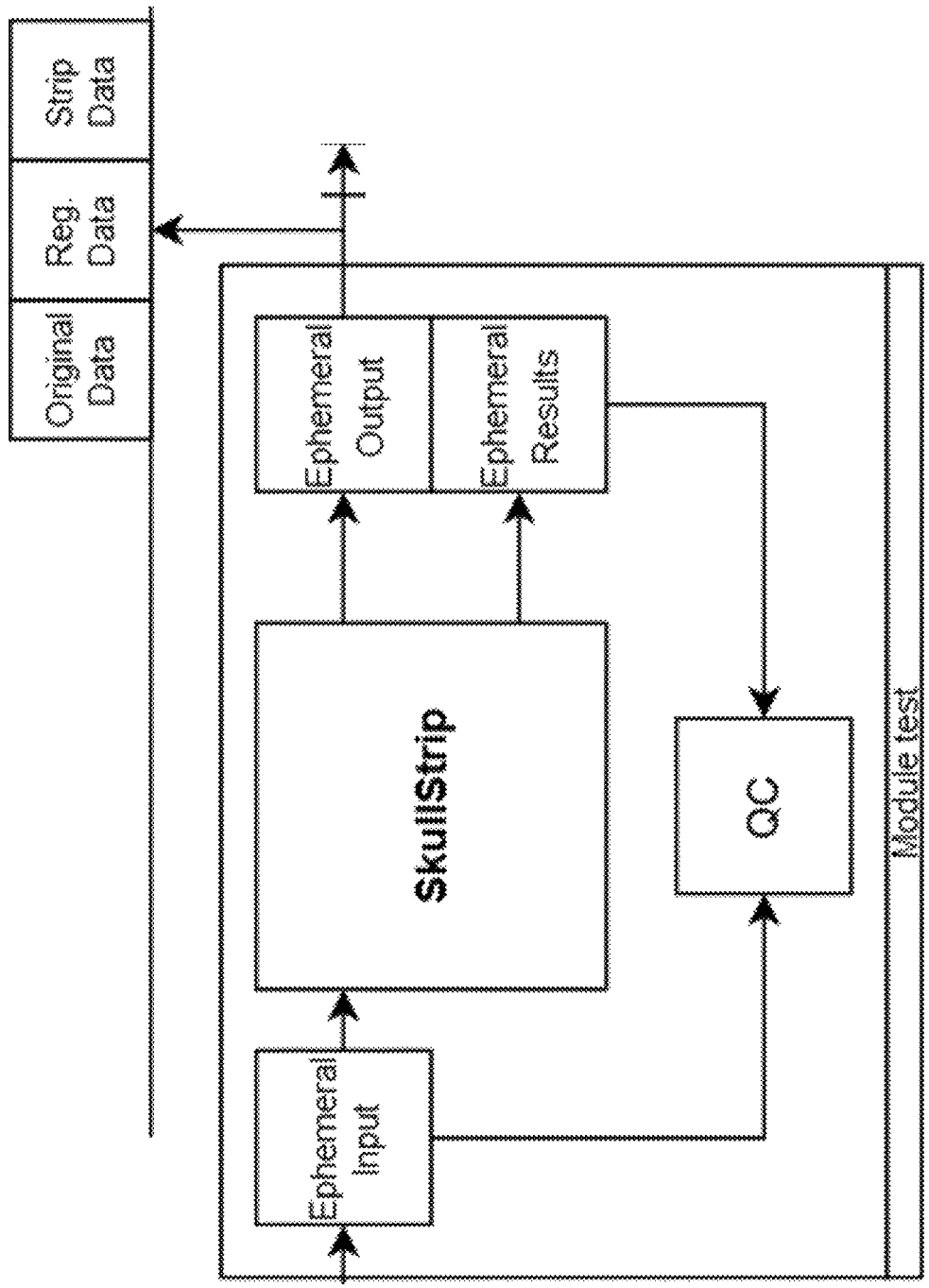
Figure 2D:
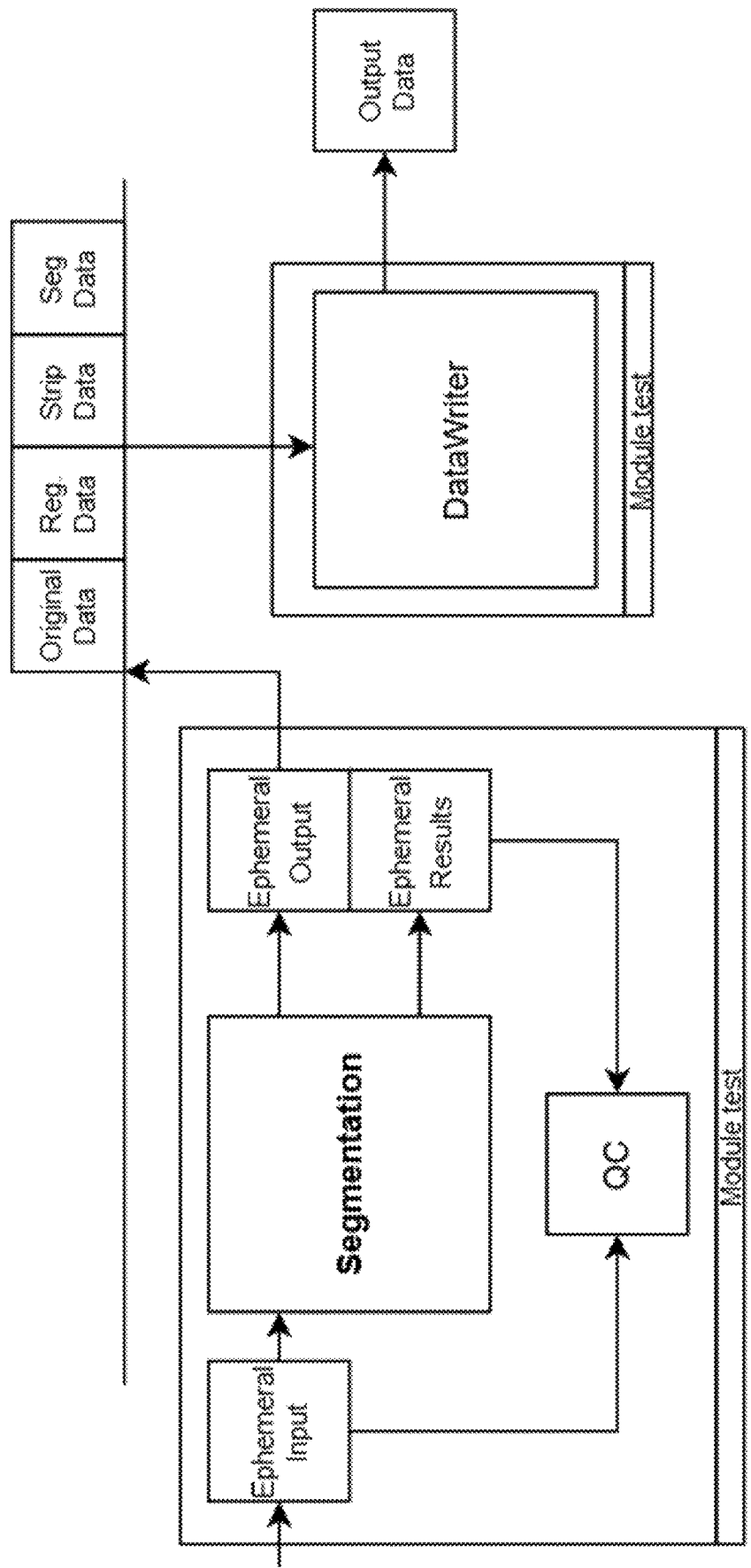

In various embodiments, the disclosure provides a deep learning convolution neural network (CNN) configured to identify, segment, and perform volumetric analysis of different tumor compartments for RANO assessment of high-grade brain gliomas on pre-operative and/or post-operative MRIs. In various embodiments, the CNN may evaluate and quantify high-grade brain glioma (grade III and IV) in magnetic resonance (MR) images that are pathologically confirmed to have brain tumors. In various embodiments, the disclosed system may reduce the time required to perform RANO analysis by 95%, e.g., to only 3-5 minutes, and the system may perform this analysis consistently, eliminating inter-rater variability of manual segmentation. FIGS. 2A-2D illustrate an exemplary segmentation data pipeline as will be described below.

In various embodiments, the system includes a cloud-based image processing software as a medical device (SaMD) configured for labeling, visualization, and volumetric quantification of tumors (e.g., high-grade brain glioma) from a set of standard MRI images in DICOM (Digital Imaging and Communications in Medicine) format. In various embodiments, semi-automatic or automatic segmentation of tumor and labeling of the tumor subcomponents form the bases for the volumetric quantification measurement output. In various embodiments, the software may include features for user log-in, viewing, loading, saving images, selecting patients from a worklist, and generating reports. In various embodiments, the report may include images, measurements, as well as previous tumor (e.g., high-grade glioma) measurements, if available, for the reviewing clinician's reference and ease of comparison.

In various embodiments, three-dimensional (i.e., volumetric) segmentation may be performed by the convolutional neural network on routinely-acquired MRI sequences. In various embodiments, the MRI sequences may include T1-weighted pre-contrast (T1) images. In various embodiments, the MRI sequences may include T2-weighted (T2) images. In various embodiments, the MRI sequences may include T1-weighted with contrast (T1c) images. In various embodiments, the MRI sequences may include Fluid Attenuated Inversion Recovery (FLAIR) images. In various embodiments, the MRI sequences may include at least one of each sequence type (e.g., T1, T2, T1, and FLAIR) for each MRI image slice of the head. In various embodiments, the MRI sequences may include four images per slice—one of each of T1, T2, T1, and FLAIR. In various embodiments, the MRI sequences may be normalized through pre-processing modules. In various embodiments, the MRI sequences may be analyzed (with or without pre-processing) via the deep learning algorithm, such as the CNN as described in more detail below.

In various embodiments, the system may segment the post-surgical cavity, residual tumor volume (RTV), and/or Organs At Risk (OAR) on post-operative MRIs prior to subsequent treatment. In various embodiments, the system may be used to segment any suitable anatomical structure, condition, or disease, including, but not limited to, glioma, brain metastases, multiple sclerosis, stroke, etc.

In various embodiments, the disclosed workflow includes semi-automatic or automatic segmentation of a tumor (e.g., high-grade glioma), labeling of the tumor subcomponents, and/or volumetric calculation of subcomponents of the tumor as described below. In various embodiments, the workflow may be performed on pre- and/or post-operative MRIs. In various embodiments, the workflow receives four different MRI sequences (i.e., T1 pre-contrast, T1 post-contrast, T2 and FLAIR) as input. In various embodiments, the workflow may perform post-processing. In various embodiments, the workflow may produce as output labelled MRI images. In various embodiments, the labelled MRI images may contain color-coded segmentation maps and volumetric measurement of the various tumor sub-components on pre-operative MRIs (e.g., enhancing tumor, edema, and/or necrosis) and/or post-operative MRIs (e.g., enhancing tumor, edema, resection cavity, and/or necrosis).

In various embodiments, a resection cavity may be defined as the region within the surgical resection that is of high intense (bright) or heterogenous signal on T2w and FLAIR images, low intense (dark) or heterogenous signal on T1w images and is non-enhancing on the post-contrast T1w images.

Figure 6:
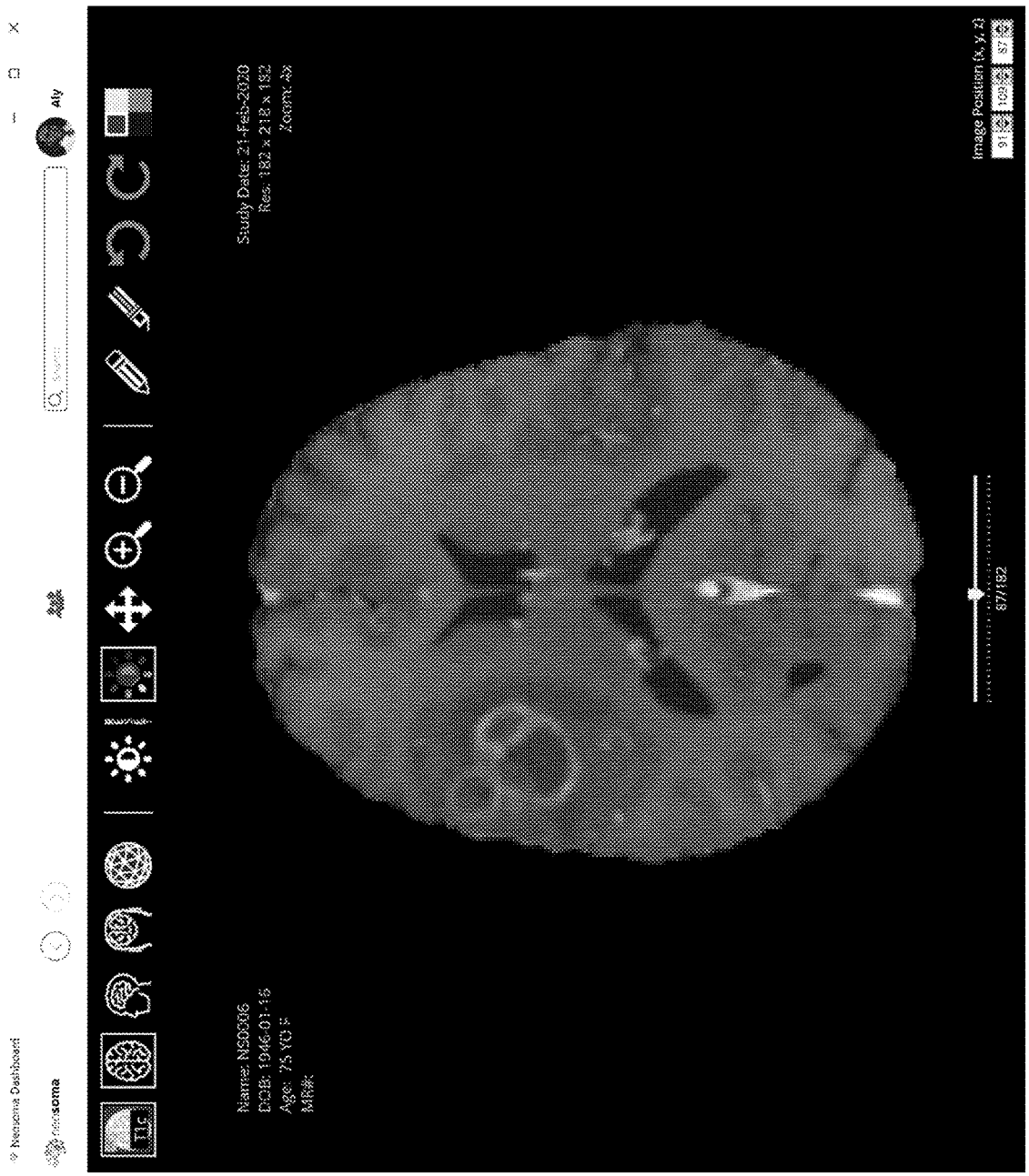
FIG. 6 illustrates an exemplary graphical user interface for viewing medical images and tumor segmentations according to embodiments of the present disclosure.

In various embodiments, the disclosed system may support visualization, quantification, and/or data-reporting functionalities. In various embodiments, visualization may be provided in the form of a built-in viewer interface that allows for: 2D image review of the MRI images for all four sequences (i.e., T1 pre-contrast, T1 post-contrast, T2 and FLAIR); and 2D review of images with color-coded mapping of sub-components overlay. In various embodiments, as shown in FIG. 6, the visualization may include various image navigation tools as are known in the art. For example, the interface may include zoom in/out, change in image orthogonality (e.g., where the images may be reformatted to display in axial, coronal, and sagittal planes), slice scroll, and/or adjusting opacity level of the color-coded mapping overlay. Various image navigation tools are displayed along the top bar of FIG. 6. In various embodiments, the visualization may include 3D image rendering that allow for: combination of multiple slices of 2D images to render a single image with depth information. In various embodiments, the 3D image may be used only for visualization purposes and not in image segmentation. In various embodiments, the 3D rendered image may not be generated using any machine learning or deep learning methodology.

In various embodiments, the visualization interface may be configured to visualize, annotate, and manipulate images.

In various embodiments, pre-existing images of a tumor (e.g., high-grade brain glioma) acquired with standard brain tumor MRI protocols may be uploaded into the system for analysis. In various embodiments, the workflow may require two or more (e.g., four) different MRI sequences (i.e., T1 pre-contrast, T1 post-contrast, T2 and FLAIR) as an input. In various embodiments, the workflow may output post-processed images containing color-coded segmentation maps and volumetric data of the tumor as a whole and/or the various tumor sub-components. In various embodiments, the segmentation of the tumor and/or the individual tumor subcomponents may be based on deep learning methodology and the segmentations may be user modifiable. In various embodiments, a color-coded mapping may identify the pre-defined subcomponents. In various embodiments, results may be displayed in the visualization interface. In various embodiments, optionally, the system may connect to clinicians' applications (e.g., PACS, EMR, DICOM viewer software, etc.).

In various embodiments, the system may perform quantification of the various tumor subcomponents. In various embodiments, the system may provide semi-automatic segmentation of brain high-grade glioma and volumetric measurements of glioma sub-components on MRI. In various embodiments, the volumetric quantifications may be based on the semi-automatic segmentation of brain glioma on MRI. In various embodiments, the system uses deep learning methodology to identify the brain glioma and label the sub-components. In various embodiments, the tumor sub-components on pre-operative MRIs may include at least one of: enhancing tumor, edema, and/or necrosis. In various embodiments, the tumor sub-components on post-operative MRIs may include at least one of: enhancing tumor, edema, resection cavity, and/or necrosis.

In various embodiments, the system may apply a single deep learning model (e.g., CNN) to output the one or more of the different tumor subcomponents. In various embodiments, the single deep learning model may be applied to either one of, or both, pre- and post-operative MRIs. In various embodiments, the measurements (e.g., volume) of the various tumor subcomponents may be determined based on the resulting segmentation from the deep learning model. In various embodiments, the segmentations are user-modifiable. In various embodiments, if a user modifies a segmentation output of the system, the system may recalculate the measurements (e.g., volume). In various embodiments, if a user modifies the segmentation, the modified segmentation may be used to retrain the deep learning model. For example, the modified segmentation may be added to the training data set and/or one or more prior segmentations may be removed from the training set.

Figure 7A:
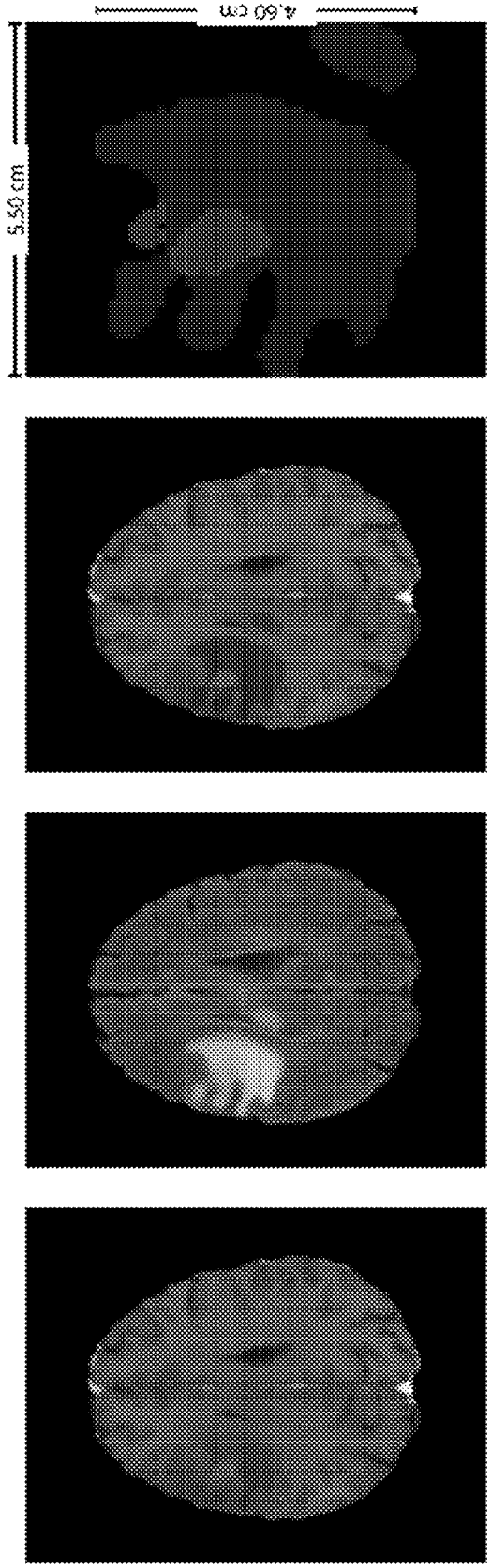
FIGS. 7A-7B illustrate an exemplary report generated by a tumor segmentation system according to embodiments of the present disclosure.
Figure 7B:
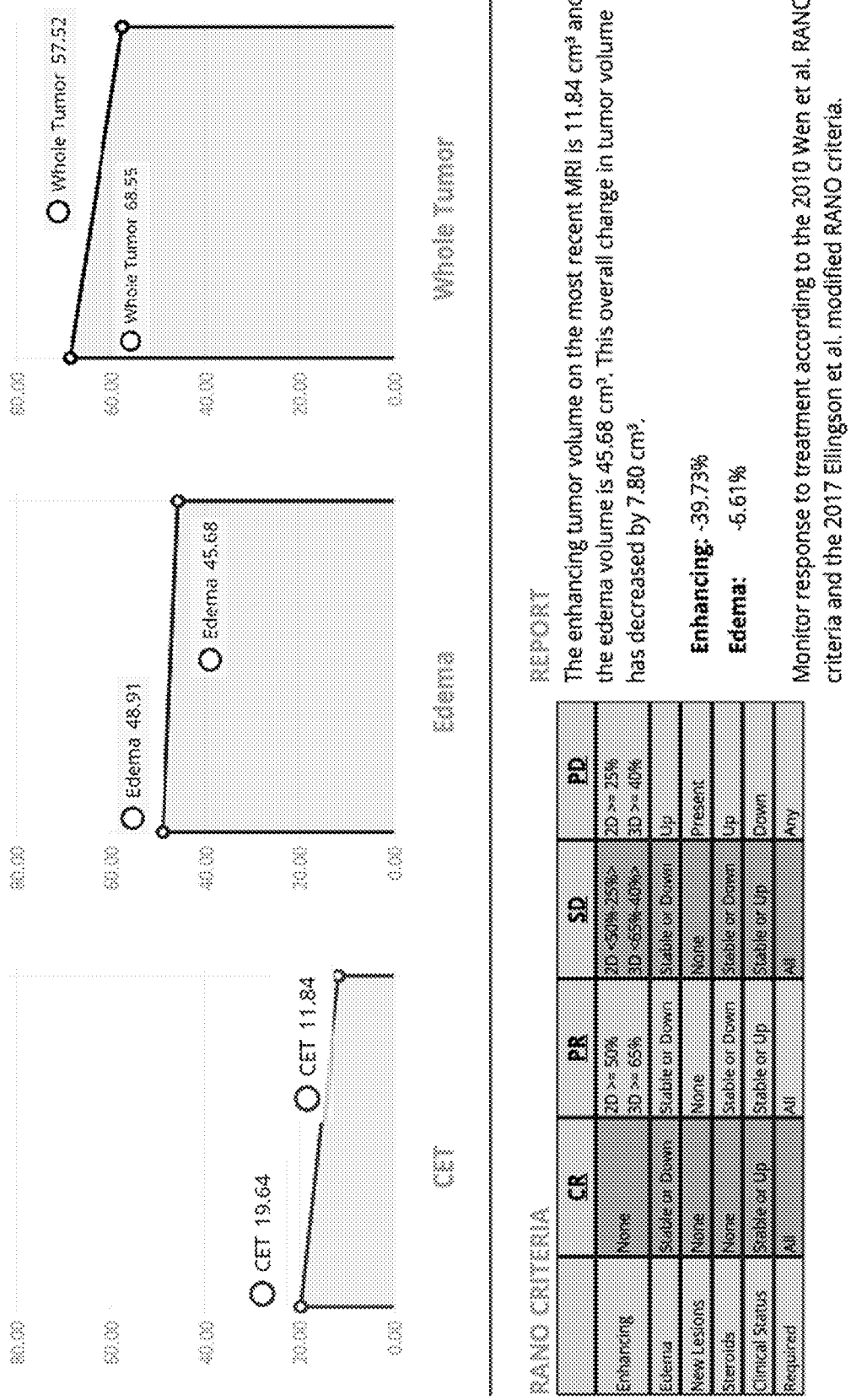

In various embodiments, the system may be configured to perform data reporting such that a user (e.g., healthcare professional) may easily interpret the outputs of the system. In various embodiments, the measurements (e.g., volume) of glioma sub-components along with segmentation overlay may be displayed to the user within a client web browser or a native application. In various embodiments, the user is provided with an option to create a pdf report of the data or save the data for later use, for example, for later review on a PACS workstation. In various embodiments, if the tumor volume measurements from previous studies are available, the system may display the previous measurements for the clinician's reference and/or provide a comparison of tumor size changes, as shown in FIGS. 7A-7B. The user can also send the data to the clinician database, such as PACS, for review.

In various embodiments, a user may operate the software by first selecting the patient MRI case. In various embodiments, the MRI sequences may be de-identified and transferred to a cloud server hosting the disclosed service. In various embodiments, the system identifies the different types of MRI sequences: T1-weighted (T1), T1-weighted with contrast agent (T1c), T2-weighted (T2), and/or Fluid-Attenuated-Inverse-Recovery (FLAIR) that are required for the analysis from the entire set of sequences in the MRI study. These are four standard sequences broadly used in clinical practice.

In various embodiments, the system may pre-process the four sequences across the entire MRI study. In various embodiments, the system may perform suitable intensity normalization for each type for MRI sequence, as different intensity normalization parameters may be required for each different type of MRI sequence. In various embodiments, the system may display a segmentation formed of one or more (e.g., three) labels of the tumor sub-components for the pre-operative (e.g., enhancing tumor, edema and/or necrosis) and post-operative (e.g., enhancing tumor, edema and resection cavity, and/or necrosis) images. In various embodiments, two or more of the labels may be combined into a single label. For example, the resection cavity and necrosis may be a single label.

In various embodiments, the resulting segmentation may include a segmentation map where each voxel is labeled as one of the tumor compartments. In various embodiments, the label may be based on the difference in MRI signal on all 4 sequences. In various embodiments, the segmentation result may be overlaid on the original input images to visualize the extent of the brain tumor. In various embodiments, the system may allow for exporting of the segmentation map independent of the MRI images. In various embodiments, the system may prevent the exporting of the segmentation map independent of the MRI images. In various embodiments, a learning system may learn differences in MRI signals based on a training set of ground truth images (e.g., from neuroradiologist-labelled images). In various embodiments, the intensity of the MRI at the particular voxel may be used to determine a label. In various embodiments, the intensity of the MRI at a region of voxels (e.g., an average intensity at a predetermined region, such as a segmentation region) may be used to determine a label. In various embodiments, a location of the voxel(s) may be used to determine a label. In various embodiments, relationships of one or more labels to any of the other labels may be used.

In various embodiments, a learning system (e.g., a CNN) may determine optimal labeling and categorization of voxels through its training, based on the ground truth images. In various embodiments, filters in the CNN may learn and/or maximize relationships between multiple attributes/parameters, including, but not limited to: voxel location, intensity, and/or predicted label. In various embodiments, groups of voxels of set dimensions (e.g., 3×3 or 5×5) may be convolved into a central voxel within the group. In various embodiments, during convolution of a group of voxels into a central voxel, processing of a priori input data—e.g., neighboring voxels—may be used to help distill the information. For example, filters (and the repeated filtering process throughout the CNN) may help with edge detection (e.g., between different tumor compartments or tissue types). In various embodiments, the filter processes thus may change the labeling for neighboring voxels.

In various embodiments, the segmentation results as well as the MRI sequences used for the analysis may be transferred back to the site of origin (e.g., a PACS) with the segmentation presented as a colored overlay for user (e.g., healthcare provider) review. In various embodiments, the segmentation results and MRI sequences of the MRI study may be loaded into a PACS worklist. In various embodiments, loading into a PACS worklist may be performed automatically once segmentation is complete and the results are applied to the original MRI images. In various embodiments, one or more users (e.g., reviewing healthcare providers) may be notified when the results are uploaded.

In various embodiments, the system may interface directly with MR or other image data collection equipment. In various embodiments, the system may be isolated from, and not connected to any MR or other image data collection equipment. In various embodiments, the system may receive data files (e.g., DICOM image files) previously generated by such equipment. In various embodiments, the analysis results may be available on-screen and can be saved, shared, and sent to the clinician database for review. In various embodiments, the system saves healthcare provider time by reducing (e.g., eliminating) time spent manually segmenting images and automates error-prone manual tasks.

Figure 3A:
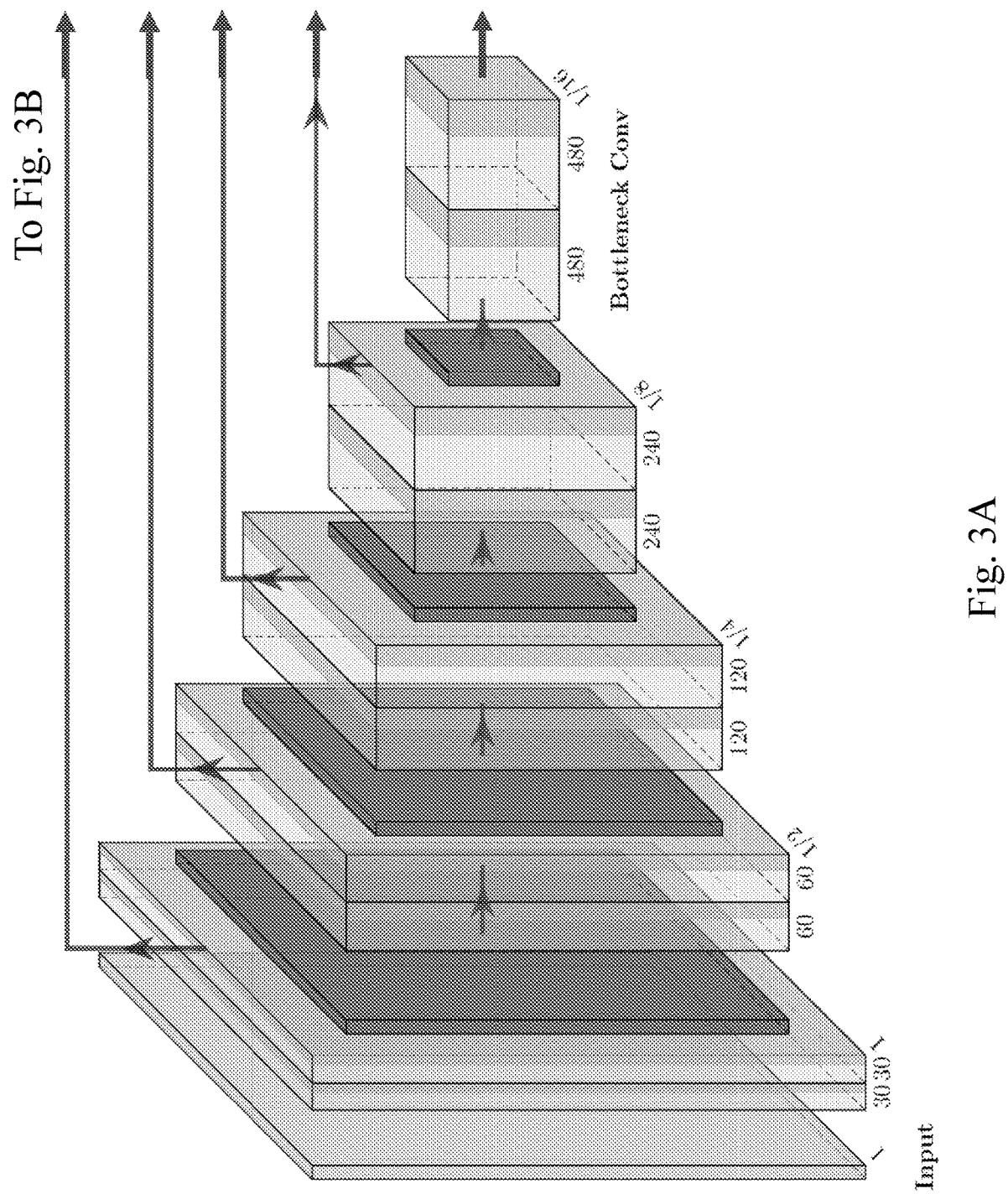
FIGS. 3A-3B illustrate an exemplary convolutional neural network (CNN) according to embodiments of the present disclosure.
Figure 3B:
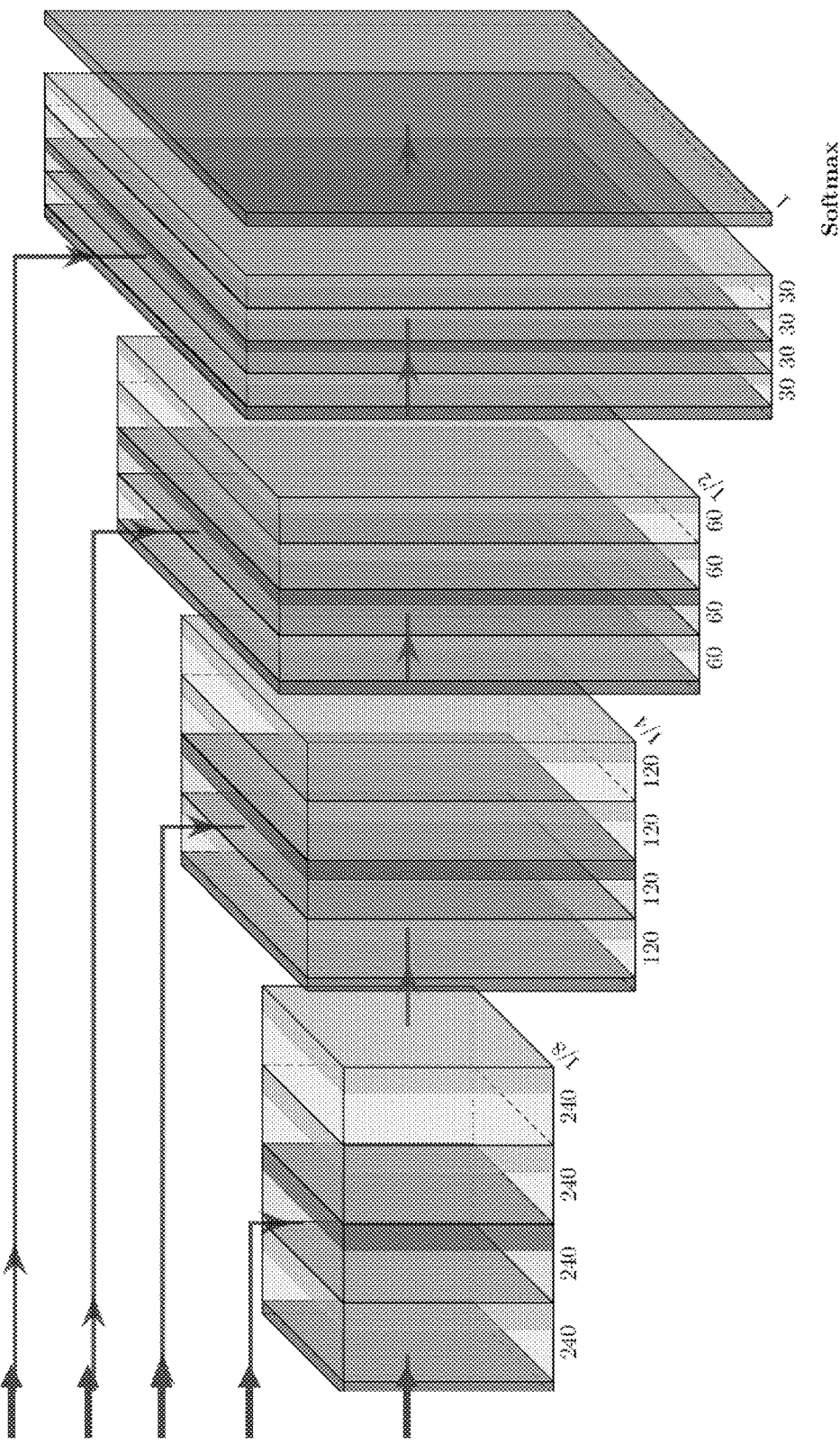

In various embodiments, as shown in FIGS. 3A-3B, the deep learning segmentation model may include a convolutional neural network. In various embodiments the convolutional neural network includes a 3D U-Net (e.g., nnU-net). In various embodiments, the convolutional neural network includes 5 sub-models, which may be trained by 5-fold cross-validation to create an ensemble model using majority voting. In various embodiments, majority voting may include where every individual sub-model votes for a class, and the majority wins. In various embodiments, in statistical terms, the predicted target label of the ensemble is the mode of the distribution of individually predicted labels. In various embodiments, the deep learning sub-models may be trained based on a partition of the training data into 70% training, 20% validation and 10% testing from a set of 557 patient studies (300 pre-operative and 257 post-operative) and a total number of 481,158 images. In various embodiments, each of the sub-models may be trained and validated using a different subset of the dataset. In various embodiments, the final testing dataset may be used for the ensemble model and may include pre-operative and post-operative cases.

In various embodiments, dropout based regularization may be used with random dropout rate of 50% across all layers of the model. In various embodiments, Adam optimization with learning rate of $3e^{-4}$ may be used. In various embodiments, data augmentation may be employed as elastic deformation with alpha [0-200] and sigma [9-13]. In various embodiments, the model may include gamma transformation of [0.7-1.5] to thereby change the mean and standard derivation of the patch. In various embodiments, the model may be configured to handle random rotations in range [−30, +30] degrees, random scale range [0.85, 1.25] and random image cropping a padding with a crop size of 128. In various embodiments, the deep learning model may provide a label mask comprising three labels: Label "0" for background/healthy tissue, label "1" for edema; label "2" for enhanced tissue; label "3" for necrosis+resection cavity.

In various embodiments, images may be anonymized to protect patient privacy in compliance with the Health Insurance Portability and Accountability Act (HIPAA). In various embodiments, the system may not interact directly with any MR scanner equipment. In various embodiments, the software operates on images (in standard DICOM format) previously generated by imaging equipment.

In various embodiments, the model training dataset may be generated using patient studies. In various embodiments, the patient studies used for ground truth (GT) creation and training includes de-identified/anonymized data set (e.g., 557 patient MRI studies including 300 pre-operative and 257 post-operative MRIs) and images from 2 main sources (e.g., a total number of 481,158). For example, the images may be collected from public patients MRI studies with pathology proven high grade glioma cases from the publicly available "The Cancer Imaging Archive." In another example, images may be collected from private company-owned patients MRI studies with pathology proven high grade glioma acquired from our collaborating clinical sites. In various embodiments, the patient MRIs may be selected to be included in the training dataset if the patient matches qualifying criteria, for example, if the patient is 18 years or older with pathology proven high grade glioma and the MRIs met the imaging criteria of the Standardized Brain Tumor Imaging Protocol.

The following table illustrates the training dataset sites, number of patient MRI studies and the wide variety of MRI scanners that were used to acquire the patient MRIs:

| Public | Name | Sites | Number of patients | Scanners |
|---|---|---|---|---|
| | TCGA-GBM | 8 sites | 335 | GE; Genesis 1.5, Signa 1.5 T & 3 T Siemens; Trio 3 T, Symphony 1.5 T, Avanto 1.5 T, Magnetom 1.5 T, Skyra 3 T Philips; Intera 1.5 T & 3 T, Achieva 1.5 T & 3 T, Ingenia 1.5 T |
| | TCIA-Brain Tumor Progression | Not reported | 20 | Not reported |
| | ACRIN-FMISO-BRAIN (ACRIN- | 3 sites | 59 | 1.5 or 3 T scanners (Philips 3 T, GE 3 T, Siemens 3 T, and Siemens 1.5 T) |
| | ACRIN-DSC-BRAIN (ACRIN 6677) | 24 sites | 83 | 1.5 or 3 T scanners (Siemens and GE) |

In various embodiments, dataset ground truthing (GT) may be determined using one or more expert annotators. For example, five (5) different radiologists with 3+ years of experience in neuroradiology created the initial GT on each MRI, i.e., one neuroradiologist per MRI case. In various embodiments, the GT may include the one or more of the three pre-operative labels (e.g., Enhancing, Edema and Necrosis) on pre-op MRIs, and/or one or more of the three postoperative labels (e.g., Enhancing, Edema, and Necrosis+Resection Cavity) on the post-op MRIs needed for training. In this example, one (1) radiologist with 5+ years of experience in neuroradiology reviewed, corrected, and approved each ground truth segmentation. In various embodiments, the final GT and corresponding MRIs may be used for training the single deep learning model to analyze pre- and post-operative brain glioma MRIs.

Figure 4:
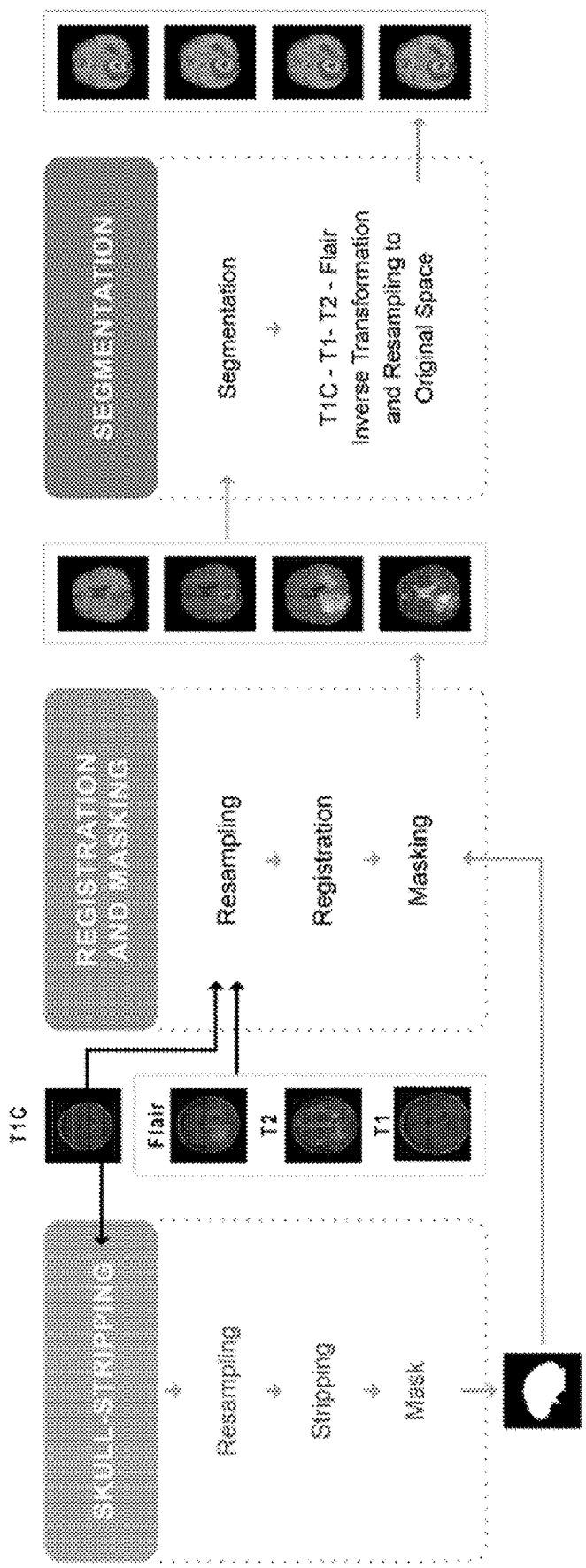
FIG. 4 illustrates an exemplary segmentation workflow according to embodiments of the present disclosure.

In various embodiments, the dataset distribution may be randomly divided between training, testing, and validation. In various embodiments, the ground-truth images may be randomly divided into training (70%), validation (20%) and testing (10%) data sets. In various embodiments, all associated images for a patient may be added to the corresponding set. In various embodiments, the segmentation algorithm may include a pre-trained algorithm and a further trained and optimized algorithm. In various embodiments, the optimized model may be trained using training data from a base algorithm (trained on only that set of training data) supplemented with additional data and labels that are not present in the training data for the base algorithm. In various embodiments, the single segmentation algorithm processes both pre-operative and post-operative MRIs. In various embodiments, the input images include T1w pre-contrast, T1w post-contrast, T2w, and FLAIR sequences. In various embodiments, the images are pre-processed (e.g., co-registered, intensity normalized, and skull stripped), then segmented and post-processed (e.g., inverse transformation of the segmentation to the original MRI space). FIG. 4 illustrates an exemplary segmentation workflow including these steps.

In various embodiments, the data set of the pre-trained algorithm may include: 1. A single-institutional retrospective dataset with 694 MRI examinations from 495 patients; 2. A multi-institutional clinical trial dataset with 2034 MRI examinations from 532 patients acquired across 34 institutions; 3. A single-institutional retrospective dataset with 492 MRI examinations from 423 patients undergoing routine MRI at different stages of the disease (including 79 early postoperative MRI scans acquired <72 h after surgery).

In various embodiments, the further trained and optimized algorithm may include additional training with 557 patients MRI studies (300 pre-operative and 257 post-operative MRIs with a total number of 481,158 images and up to 700 epochs). In various embodiments, the new training data may include one or more additional labels. For example, the further trained and optimized algorithm may include the additional pre-operative label "necrosis" and the additional post-operative label "necrosis+resection cavity."

In various embodiments, NS-HGlio is 3D U-Net based and consists of 5 sub-models, which are trained by the concept of a 5-fold cross-validation to create an ensemble model using majority voting. The majority voting design is where every individual sub-model vote for a class, and the majority wins. In statistical terms, the predicted target label of the ensemble is the mode of the distribution of individually predicted labels.

In various embodiments, as shown in FIGS. 3A-3B, the deep learning architecture includes a modified version of the nnU-Net. In various embodiments, the left side of the U-Net architecture includes an encoder portion, the middle includes a bottleneck portion, and the right includes a decoder portion. In various embodiments, the decoder portion may include skip-connections. In various embodiments, the number of feature channels "I" indicates the feature map dimensionality with an original patch size of (128×128×128). As shown in FIGS. 3A-3B, the encoder structure (to the left of the bottleneck convolutional layer) includes:

| Layer name | Feature channels, 3D feature map dimension |
|---|---|
| Input patch image | (4, 128, 128, 128) |
| 3 × 3 × 3 Convolutional layer & Leaky ReLU | (30, 128, 128, 128) |
| 3 × 3 × 3 Convolutional layer & Leaky ReLU | (30, 128, 128, 128) |
| 2 × 2 × 2 Maxpool layer | (4, 64, 64, 64) |
| 3 × 3 × 3 Convolutional layer & Leaky ReLU | (60, 64, 64, 64) |
| 3 × 3 × 3 Convolutional layer & Leaky ReLU | (60, 64, 64, 64) |
| 2 × 2 × 2 Maxpool layer | (4, 32, 32, 32) |
| 3 × 3 × 3 Convolutional layer & Leaky ReLU | (120, 32, 32, 32) |
| 3 × 3 × 3 Convolutional layer & Leaky ReLU | (120, 32, 32, 32) |
| 2 × 2 × 2 Maxpool layer | (4, 16, 16, 16) |
| 3 × 3 × 3 Convolutional layer & Leaky ReLU | (240, 16, 16, 16) |
| 3 × 3 × 3 Convolutional layer & Leaky ReLU | (30, 16, 16, 16) |
| 2 × 2 × 2 Maxpool layer | (4, 8, 8, 8) |

The bottleneck convolutional layer (latent space) includes:

| Layer name | Feature channels, 3D feature map dimension |
|---|---|
| 3 × 3 × 3 Convolutional layer & Leaky ReLU | (480, 8, 8, 8) |
| 3 × 3 × 3 Convolutional layer & Leaky ReLU | (480, 8, 8, 8) |

The decoder structure (to the right of the bottleneck convolutional layer) includes:

| Layer name | Feature channels, 3D feature map dimension |
|---|---|
| 2 × 2 × 2 Trilinear up-sampling layer | (240, 16, 16, 16) |
| Concatenation of skip connection layers | (240, 16, 16, 16) |
| 3 × 3 × 3 Convolutional layer & Leaky ReLU | (240, 16, 16, 16) |
| 3 × 3 × 3 Convolutional layer & Leaky ReLU | (240, 16, 16, 16) |
| 2 × 2 × 2 Trilinear up-sampling layer | (120, 32, 32, 32) |
| Concatenation of skip connection layers | (120, 32, 32, 32) |
| 3 × 3 × 3 Convolutional layer & Leaky ReLU | (120, 32, 32, 32) |
| 3 × 3 × 3 Convolutional layer & Leaky ReLU | (120, 32, 32, 32) |
| 2 × 2 × 2 Trilinear up-sampling layer | (30, 64, 64, 64) |
| Concatenation of skip connection layers | (30, 64, 64, 64) |
| 3 × 3 × 3 Convolutional layer & Leaky ReLU | (60, 64, 64, 64) |
| 3 × 3 × 3 Convolutional layer & Leaky ReLU | (60, 64, 64, 64) |
| 2 × 2 × 2 Trilinear up-sampling layer | (30, 128, 128, 128) |
| Concatenation of skip connection layers | (30, 128, 128, 128) |
| 3 × 3 × 3 Convolutional layer & Leaky ReLU | (30, 128, 128, 128) |
| 3 × 3 × 3 Convolutional layer & Leaky ReLU | (30, 128, 128, 128) |
| 1 × 1 × 1 Convolutional layer & Softmax | (1, 128, 128, 128) |

In various embodiments, the MRI images may be pre-processed. In various embodiments, the system may apply one or more preprocessing steps before creating the segmentation labels.

In various embodiments, these pre-processing steps may include data import/intensity normalization, registration, and/or skull stripping. In various embodiments, images may be read into memory. In various embodiments, intensity normalization may be performed to normalize image intensities in the range [0-1] on each of the four MRI modalities. In various embodiments, intensity normalization compensates for intensity differences yielded by different MRI protocols and vendors.

Figure 5A:
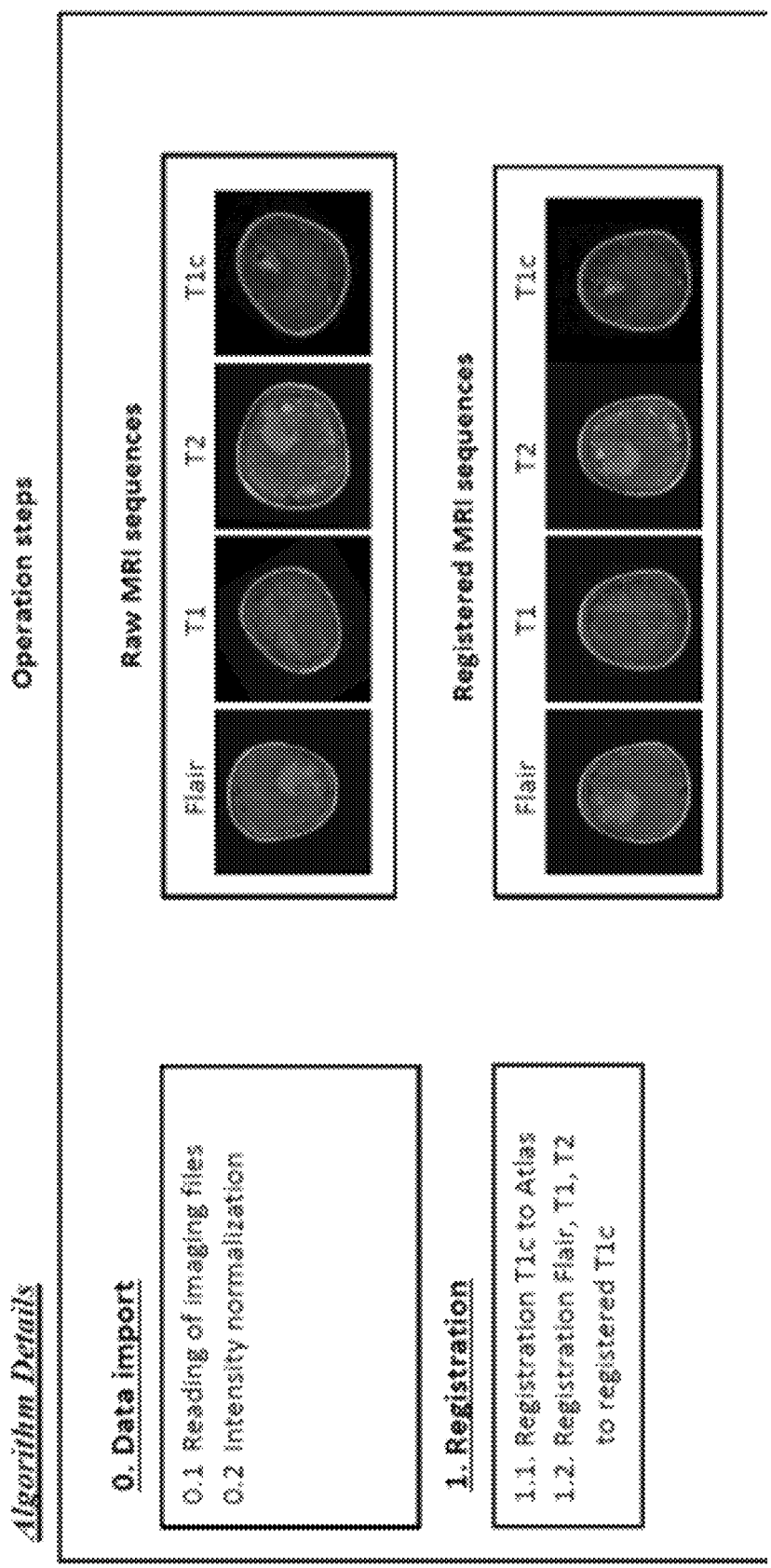
FIGS. 5A-5B illustrates an exemplary segmentation workflow according to embodiments of the present disclosure.

In various embodiments, as shown in FIG. 5A, the T1w pre-contrast sequence may be registered to a standard anatomical atlas. In various embodiments, the T1w pre-contrast images may be registered before the other images are registered. In various embodiments, the T1w pre-contrast sequence may be registered to the standard MNI atlas. In various embodiments, the FLAIR, T1w post-contrast, T2w weighted images may then be registered to the MNI registered T1w pre-contrast sequence. In various embodiments, all images may be aligned to the MNI152 space, now having the same properties as the atlas (e.g., image size, dimension, orientation, point of origin, and/or vector to the point of origin).

Figure 5B:
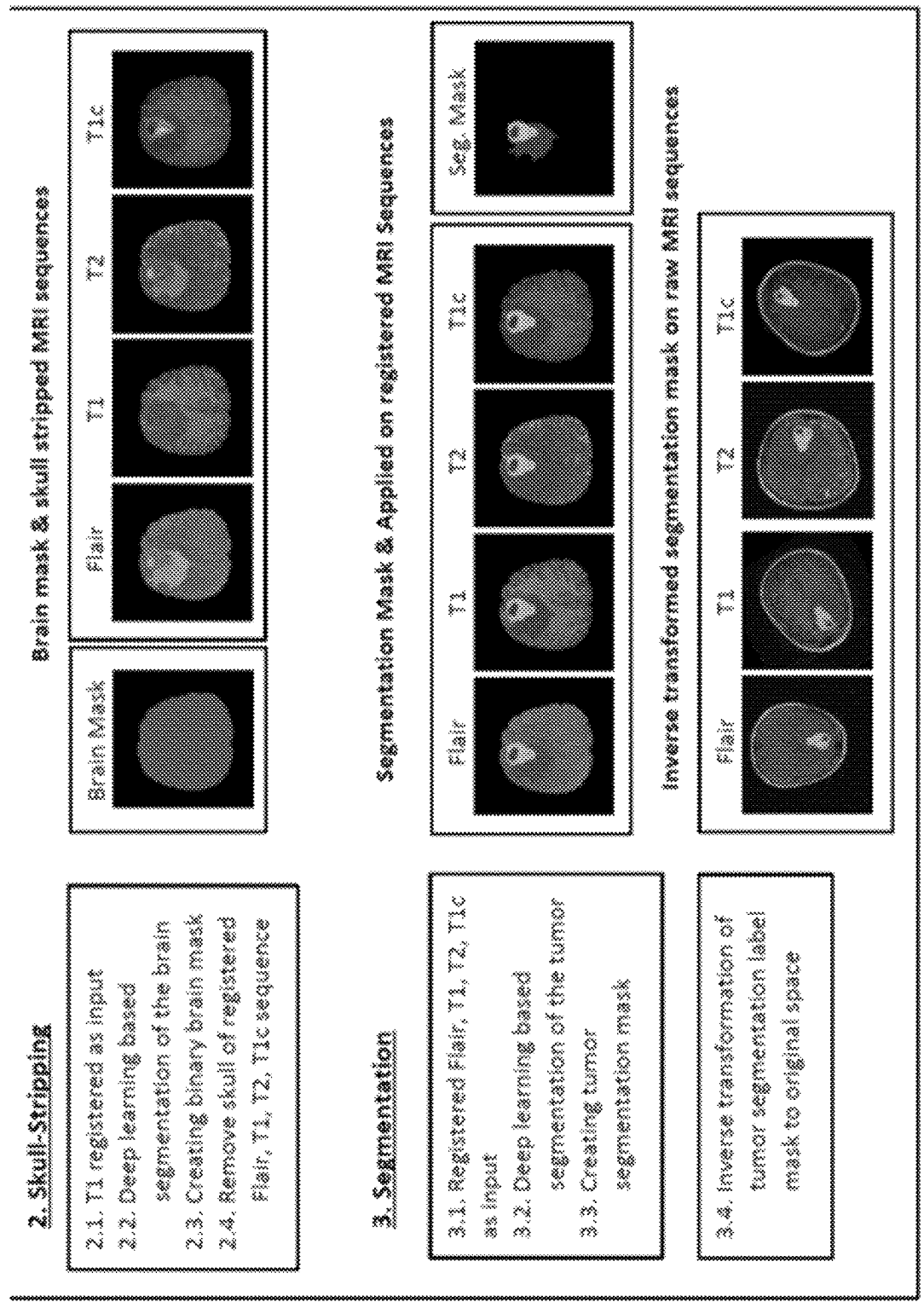

In various embodiments, as shown in FIG. 5B, any portions of the skull (e.g., bone tissue) may be removed from the MRI images via a skull stripper. In various embodiments, skull stripping may be performed using a learning system. In various embodiments, the skull stripper learning model may receive as input the registered T1w pre-contrast image. In various embodiments, the model outputs a deep learning-based skull-stripped binary mask. In various embodiments, the binary mask allows the system to separate the skull from the brain. In various embodiments, the binary mask includes a binary label where, for example, pixels associated with the skull are labelled a '0' while pixels associated with the brain are labelled a '1'. In various embodiments, the binary mask is applied to all registered modalities, namely the T1w pre-contrast, T1w post-contrast, T2 and FLAIR sequences.

In various embodiments, as shown in FIG. 5B, the deep learning segmentation model (e.g., 3D CNN) may receive as input the pre-processed (e.g., intensity normalized, registered, and skull stripped) images, e.g., the T1w pre-contrast, T1w post-contrast, T2 and FLAIR sequences. In various embodiments, the deep learning model may classify one or more labels (e.g., 3 labels including: enhancing tumor, edema, necrosis+resection cavity) through classification of the pixel intensity on the T1w pre-contrast, T1w post-contrast, T2 and FLAIR sequences. In various embodiments, pixel classification may be based on the training data. In various embodiments, the enhancing tumor may be represented as the high intense (bright) signal on the post-contrast T1w images compared to the pre-contrast T1w images. In various embodiments, edema may be represented as the non-enhancing tissue surrounding the enhancing tumor that is of high intense (bright) signal on T2w and FLAIR images. In various embodiments, necrosis may be represented as the region within the enhancing tumor that shows no enhancement and has a high intense (bright) signal on T2w images. In various embodiments, the resection cavity may be represented as the region within the surgical resection that is of high intense (bright) or heterogeneous signal on T2w and FLAIR images, low intense (dark) or heterogeneous signal on T1w images and is non-enhancing on the post-contrast T1w images.

In various embodiments, the deep learning model may output a segmentation map which contains the one or more (e.g., three) labels. In various embodiments, the labels may be color-coded to allow for visualization as an overlay on the 4 difference MRI sequences.

In various embodiments, MRI sequences may be labeled at the same time. In various embodiments, at least two (e.g., all four) sequences may be compared to decide on each voxel label. In various embodiments, a sequence may be generated containing X labels (e.g., discrete intensity values, each value representing one tumor compartment such as 1 for necrosis; 2 for enhancing; 3 for edema; etc.). In various embodiments, the sequence and/or mask may be color-coded based on the labels. In various embodiments, the sequence and/or mask may be manipulated based on the voxels and intensity values contained therein.

In various embodiments, the MRI images may be post-processed after segmentation. In various embodiments, after the segmentation is created using the pre-processed T1w pre-contrast, T1w-postcontrast, T2 and FLAIR sequences, the label maps may be resampled and re-oriented to the original sequences T1, T1c, T2, and Flair space. In various embodiments, this post-processing allows the user to view the segmentations overlaid properly over the original unprocessed sequences in the visualizer as well as on any other viewer modality/PACS system. In various embodiments, resampling of label maps may be performed by re-averaging a resulting 1×1×1 mm voxel space to the original sequence voxel dimensions.

Figure 8A:
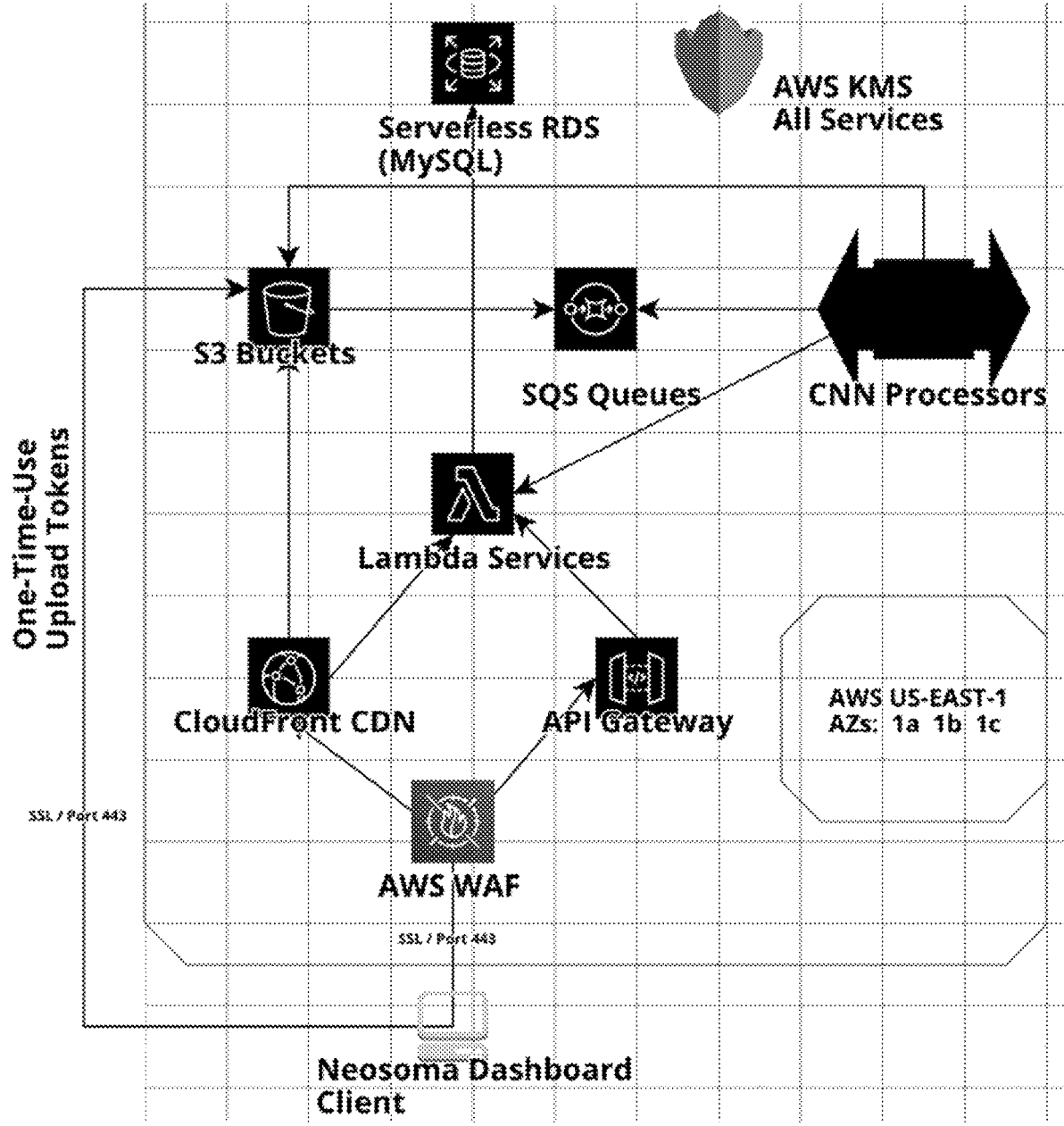
FIG. 8A illustrates an exemplary system architecture for a dashboard client according to embodiments of the present disclosure.

FIG. 8A illustrates an exemplary system architecture for a dashboard client. In various embodiments, all Client Interactions with the AWS Environment may be routed through the API Gateway or CloudFront CDN and require HTTP Authentication (or an authenticated Token from a previous request). In various embodiments, both these services may be behind an AWS WAF provisioned with applicable ACL/Rules. In various embodiments, Lambda Services can communicate with the RDS Instance using the AWS Data API. In various embodiments, all data may be encrypted at rest using AWS KMS and also in transit (typically TLS 1.2). In various embodiments, PII/PHI data may be encrypted (via AWS KMS API) at a column level protecting data from users who need direct access to the Database (DBAs/DevOps Admins). In various embodiments, all Services are supported using multiple (3) AZs to support high availability and redundancy. In various embodiments, for Software Registration, a user may install the Dashboard Client using Link provided by Account Management. In various embodiments, installation requires a valid (pre-provisioned) Hospital Name and License Registration Key. In various embodiments, Client Software validates Registration Information through API Gateway. In various embodiments, a successful response enables the user to proceed to Login/Authentication.

In various embodiments, for Login/Authentication, a user provides a Username and Password (initially provisioned with temporary password), the Client Software validates Login Information through API Gateway, all authentication requests are tracked by a Login Attempt Process, a Successful Response generates a Token that can be used for subsequent requests, a Failure Response indicates a generic failure message that the username/password was invalid, and multiple consecutive failures may result in a "locked" account. In various embodiments, for Protected Content Access, a user may provide an active authenticated Token (Base-64 Encoded) to a content endpoint behind our CloudFront URL. In various embodiments, CloudFront may route the request for Policy/Approval through our "CloudFront Authorizer"—a dedicated Lambda Service. In various embodiments, if the Token is valid and is associated to the same Hospital as the data, then the content is streamed to the client. In various embodiments, an Invalid Token returns a 403 Error to the Client. In various embodiments, for a Request for Patient Data, a user provides an active authenticated Token (Base-64 Encoded) to our API Gateway, the token is authenticated through RDS Data API to MySQL Backend, users can only access stored data for the Hospital for which the Token was generated, and Requested Patient Data is returned (HTTPS/TLS 1.2).

In various embodiments, to initiate Segmentation Processing, a user provides an active authenticated Token (Base-64 Encoded) to our API Gateway, the token is authenticated through RDS Data API to MySQL Backend, a One-Time-Use (pre-signed) Upload Token is returned to Client, the Client Software anonymizes and uploads DICOM Studies for processing direct to S3 and a successful Upload to S3 generates initiates Lambda File Validation. A Lambda Function performs initial File Validation/Conversion and record creation, confirms that all required Studies are present, converts Input format from DICOM to NIFTI, and generates SQS Message to process file. CNN Processors (monitoring the Queue) receive message and begin segmentation. Periodic Status Updates are pushed to API Gateway to inform user of progress and completed segmentation and newly Registered Images are uploaded to S3 Bucket where a Successful Upload to S3 initiates Lambda "Post Processing" function. The Lambda Function performs "final" processing, calculates and stores compartment volumes for reporting, generates Preview Images, updates a Database with "Complete" status, and sends PubNub notification that new segmentation has been completed.

Figure 8B:
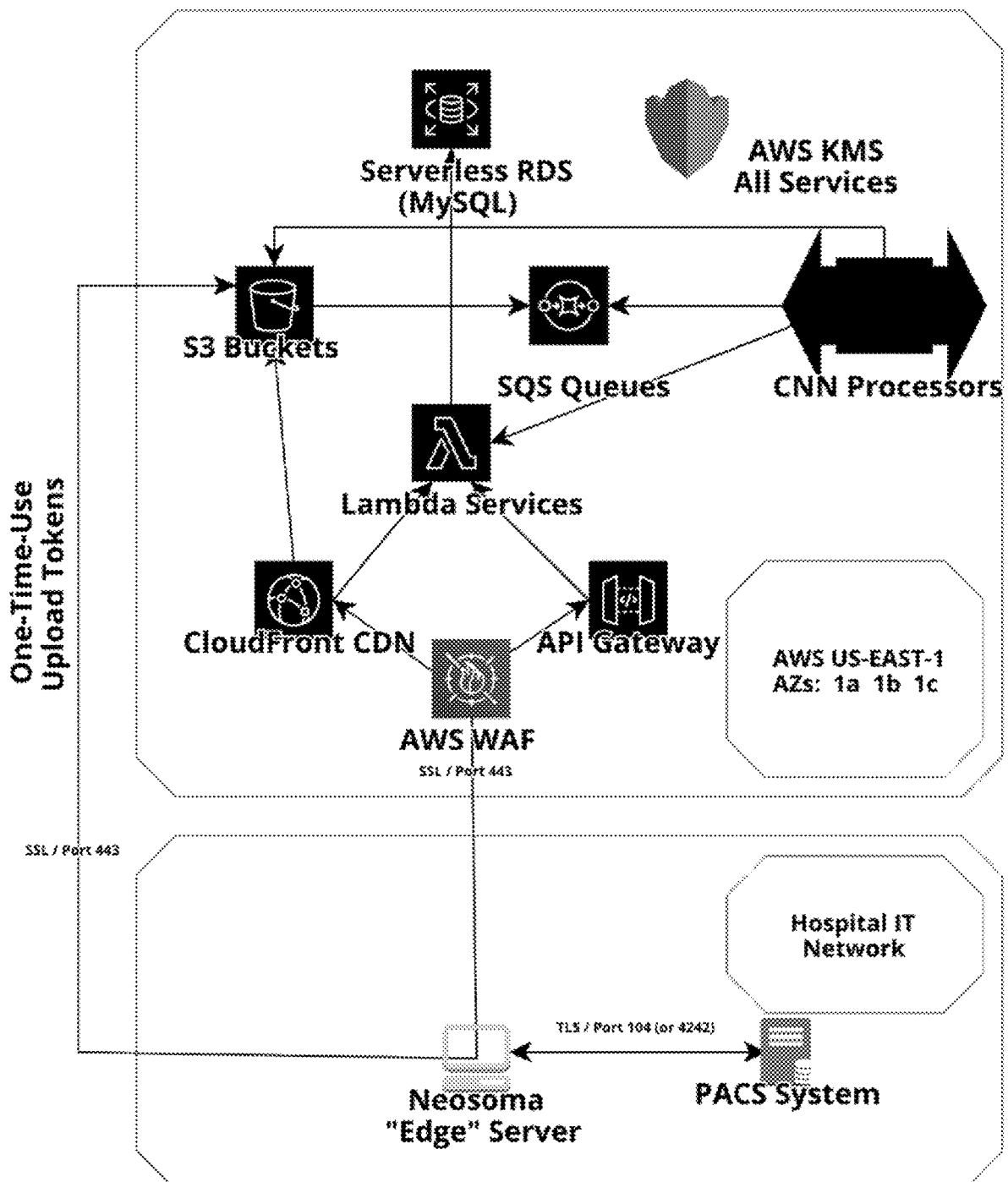
FIG. 8B illustrates an exemplary system architecture for an edge server in communication with a PACS system according to embodiments of the present disclosure.

FIG. 8B illustrates an exemplary system architecture for an edge server in communication with a PACS system. In various embodiments, the edge server architecture may be similar to the architecture of the dashboard client illustrated in FIG. 8A, where the dashboard client is replaced by the edge server and interactions are driven by the PACS system. In various embodiments, for software installation, the Edge Server is may include a Linux Docker container and may require API Credentials and some additional client configuration parameters at run time. The initial startup process will validate its access to the API Gateway. A Successful Installation will enable the Edge server to access the AWS environment specific to the configured hospital. In various embodiments, the PACS system may be configured with credentials required to connect to the Edge Server. In various embodiments, the PACS system may be configured to send acquired images which are properly tagged to the Edge Server In various embodiments, for Processing Images, as new images are acquired by the PACS with the specified Tags, the images may be sent via DICOM protocol (requires TLS) to the Edge Server. In various embodiments, the Edge Server requests a One-Time-Use (pre-signed) Upload Token from the API Gateway, the API Token is authenticated through RDS Data API to MySQL Backend, the One-Time-Use (pre-signed) Upload Token is returned to Server, a New Patient Record (if required) is created via API Gateway, the Client Software may anonymize and upload DICOM Studies for processing direct to S3 where a Successful Upload to S3 generates initiates Lambda File Validation, and the Lambda Function performs initial File Validation/Conversion and record creation. In various embodiments, the Lambda Function may confirm that all required Studies are present, convert input format from DICOM to NIFTI, and generate SQS Message to process the file. In various embodiments, the CNN Processors (monitoring the Queue) receive the message and begin segmentation, and periodic Status Updates may be pushed to API Gateway to inform user of progress. In various embodiments, the completed segmentation and newly Registered Images are uploaded to S3 Bucket where a successful upload to S3 initiates Lambda Post Processing function. In various embodiments, the Lambda Function performs final processing where compartment volumes are calculated and stored for reporting, Preview Images are generated, one or more Databases are updated with Complete status, a PubNub notification may be sent that new segmentation has been completed, and the studies can now be downloaded and viewed within the Dashboard Client.

In various embodiments, the edge server is optionally configured to poll for Completed Images. In various embodiments, the Edge Server routinely polls the API Gateway requesting recently processed image content for the installed hospital. In various embodiments, when new segmented images are detected the Edge Server will authenticate to the CloudFront CDN (behind the AWS WAF and CF Authorizer) and request the processed images. In various embodiments, processed images can then be pushed to the PACS system using the credentials provisioned during installation.

Figure 9:
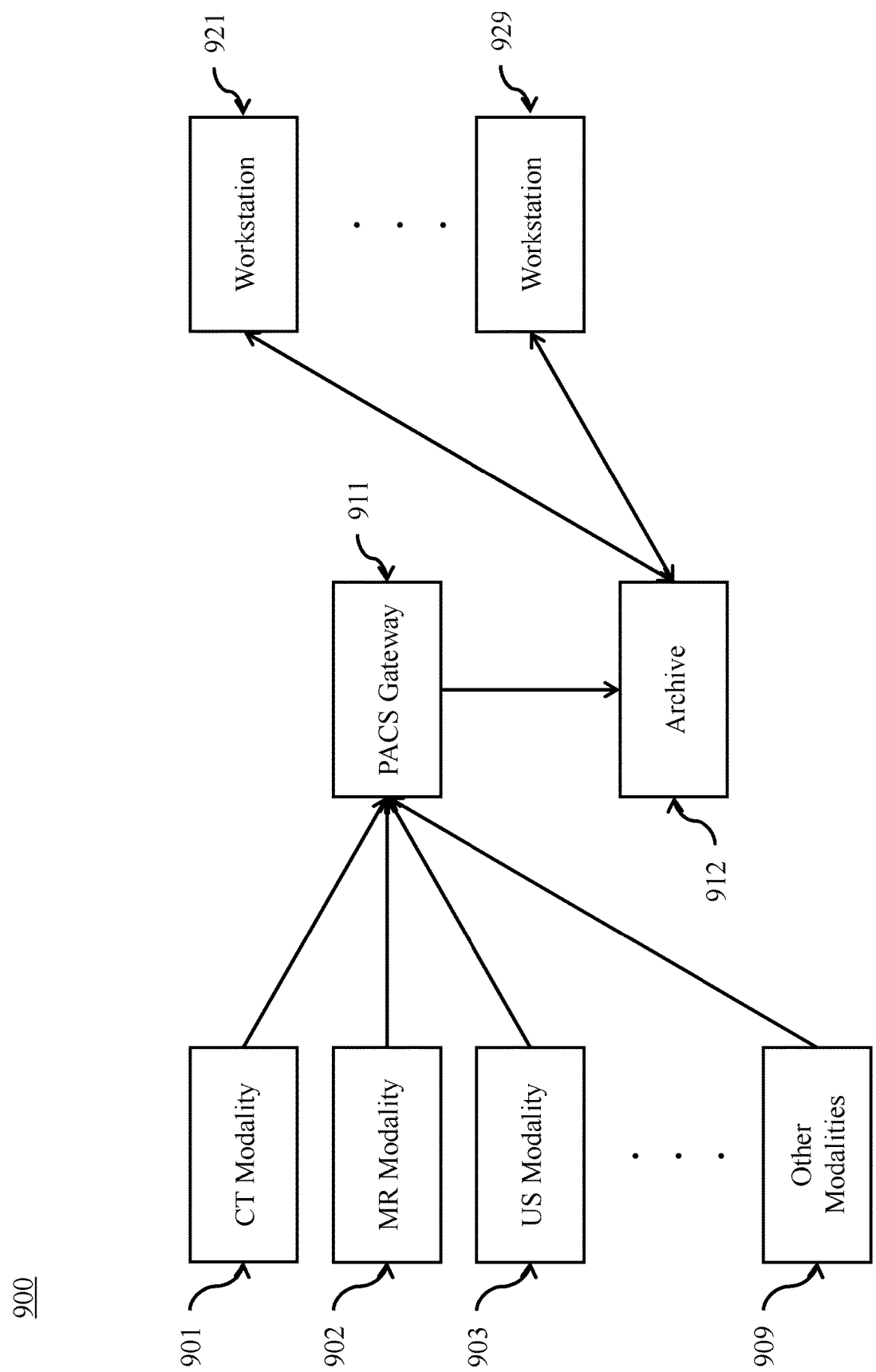
FIG. 9 depicts an exemplary Picture Archiving and Communication System (PACS).

Referring to FIG. 9, an exemplary PACS 900 consists of four major components. Various imaging modalities 901 . . . 909 such as computed tomography (CT) 901, magnetic resonance imaging (MRI) 902, or ultrasound (US) 903 provide imagery to the system. In some implementations, imagery is transmitted to a PACS Gateway 911, before being stored in archive 912. Archive 912 provides for the storage and retrieval of images and reports. Workstations 921 . . . 929 provide for interpreting and reviewing images in archive 912. In some embodiments, a secured network is used for the transmission of patient information between the components of the system. In some embodiments, workstations 921 . . . 929 may be web-based viewers. PACS delivers timely and efficient access to images, interpretations, and related data, eliminating the drawbacks of traditional film-based image retrieval, distribution, and display.

A PACS may handle images from various medical imaging instruments, such as X-ray plain film (PF), ultrasound (US), magnetic resonance (MR), Nuclear Medicine imaging, positron emission tomography (PET), computed tomography (CT), endoscopy (ES), mammograms (MG), digital radiography (DR), computed radiography (CR), Histopathology, or ophthalmology. However, a PACS is not limited to a predetermined list of images, and supports clinical areas beyond conventional sources of imaging such as radiology, cardiology, oncology, or gastroenterology.

Different users may have a different view into the overall PACS system. For example, while a radiologist may typically access a viewing station, a technologist may typically access a QA workstation.

In some implementations, the PACS Gateway 911 comprises a quality assurance (QA) workstation. The QA workstation provides a checkpoint to make sure patient demographics are correct as well as other important attributes of a study. If the study information is correct the images are passed to the archive 912 for storage. The central storage device, archive 912, stores images and in some implementations, reports, measurements and other information that resides with the images.

Once images are stored to archive 912, they may be accessed from reading workstations 921 . . . 929. The reading workstation is where a radiologist reviews the patient's study and formulates their diagnosis. In some implementations, a reporting package is tied to the reading workstation to assist the radiologist with dictating a final report. A variety of reporting systems may be integrated with the PACS, including those that rely upon traditional dictation. In some implementations, CD or DVD authoring software is included in workstations 921 . . . 929 to burn patient studies for distribution to patients or referring physicians.

In some implementations, a PACS includes web-based interfaces for workstations 921 . . . 929. Such web interfaces may be accessed via the internet or a Wide Area Network (WAN). In some implementations, connection security is provided by a VPN (Virtual Private Network) or SSL (Secure Sockets Layer). The client side software may comprise ActiveX, JavaScript, or a Java Applet. PACS clients may also be full applications which utilize the full resources of the computer they are executing on outside of the web environment.

Communication within PACS is generally provided via Digital Imaging and Communications in Medicine (DICOM). DICOM provides a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format.

DICOM groups information into data sets. For example, a file containing a particular image, generally contains a patient ID within the file, so that the image can never be separated from this information by mistake. A DICOM data object consists of a number of attributes, including items such as name and patient ID, as well as a special attribute containing the image pixel data. Thus, the main object has no header as such, but instead comprises a list of attributes, including the pixel data. A DICOM object containing pixel data may correspond to a single image, or may contain multiple frames, allowing storage of cine loops or other multi-frame data. DICOM supports three- or four-dimensional data encapsulated in a single DICOM object. Pixel data may be compressed using a variety of standards, including JPEG, Lossless JPEG, JPEG 2000, and Run-length encoding (RLE). LZW (zip) compression may be used for the whole data set or just the pixel data.

Figure 10:
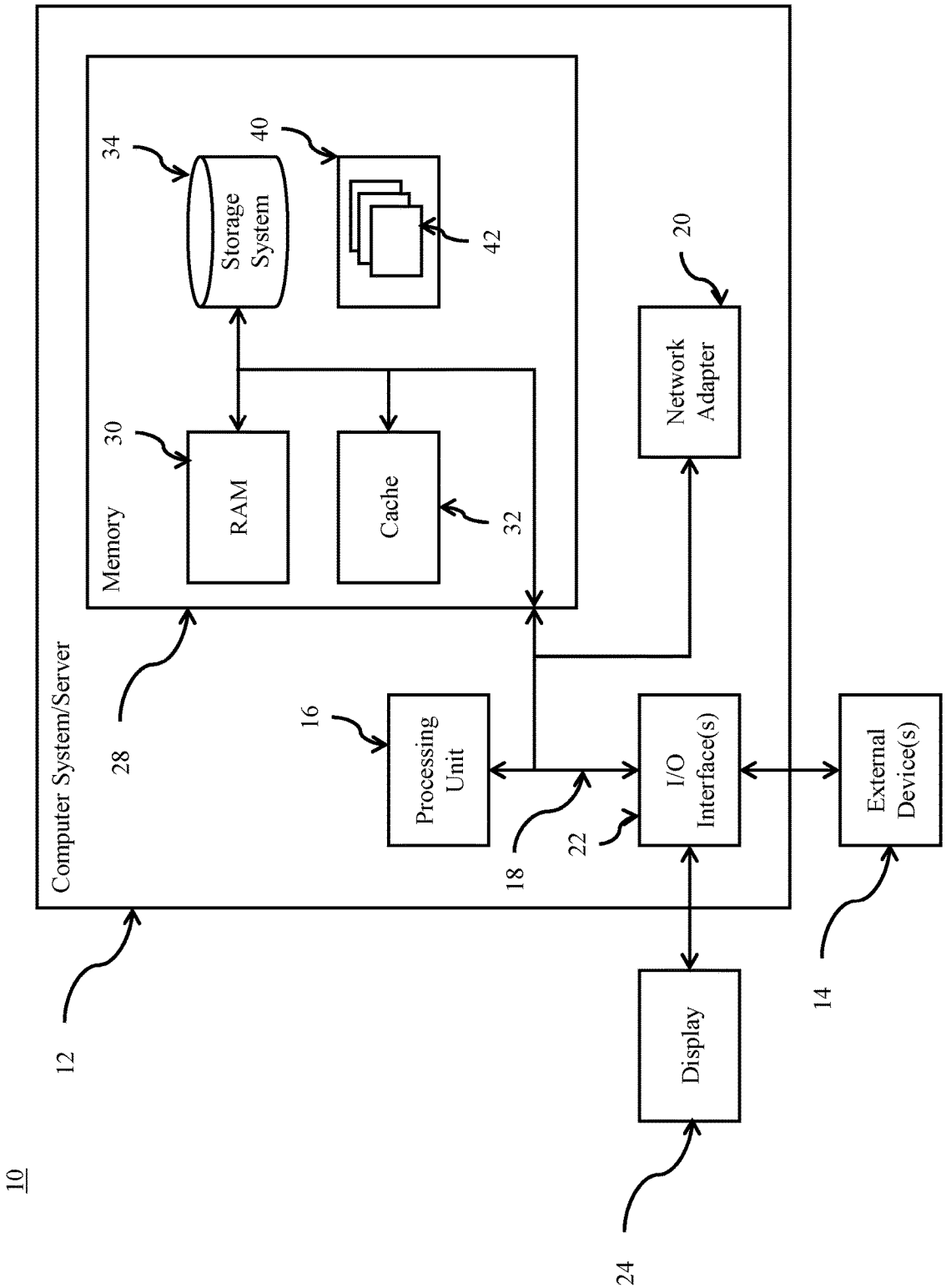
FIG. 10 depicts an exemplary computing node according to embodiments of the present disclosure.

Referring now to FIG. 10, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 10, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention. Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
receiving a plurality of magnetic resonance imaging (MRI) sequences of a head of a patient, wherein each MRI sequence comprises one or more of: a T1-weighted with contrast image, a Fluid Attenuated Inversion Recovery (FLAIR) image, a T1-weighted without contrast image, a T2-weighted image, a diffusion weighted image, a diffusion tensor image, or a perfusion image;
registering each image of the plurality of MRI sequences to an anatomical atlas, wherein registering comprises:
registering the T1-weighted with contrast image or the T1-weighted without contrast image to the anatomical atlas; and
registering the FLAIR image, T2-weighted image, diffusion weighted image, diffusion tensor image, and/or perfusion image to a corresponding registered T1-weighted with contrast image or T1-weighted without contrast image;
generating a plurality of modified MRI sequences by removing a skull from each registered image in the plurality of MRI sequences;
segmenting a tumor within a brain in each image in the plurality of modified MRI sequences, wherein segmenting the tumor includes classifying one or more tumor subcomponents of the tumor based on a comparison between pixel intensities of each image in the plurality of modified MRI sequences;
quantifying the one or more tumor subcomponents; and
outputting a volumetric measurement of the one or more subcomponents.

2. The method of claim 1, wherein each MRI sequence comprises a T1-weighted with contrast image or a T1-weighted without contrast image, and wherein generating the plurality of modified MRI sequences comprises:
segmenting the registered T1-weighted with contrast image or the registered T1-weighted without contrast image to thereby generate a binary mask identifying the brain and the skull; and
applying the binary mask to the other registered T1-weighted image, FLAIR image, T2-weighted image, diffusion weighted image, diffusion tensor image, and perfusion image thereby removing the skull from the registered images.

3. The method of claim 1, wherein the registered images correspond to a same slice of the head for each MRI sequence.

4. The method of claim 1, wherein the plurality of MRI sequences are pre-operative MRI sequences.

5. The method of claim 1, wherein the plurality of MRI sequences are post-operative MRI sequences.

6. The method of claim 1, wherein the tumor subcomponents comprise at least one of an enhancing tumor, an edema, a resection cavity, and a necrosis.

7. The method of claim 1, further comprising normalizing an intensity of the images in the plurality of MRI sequences.

8. The method of claim 1, wherein segmenting the tumor comprises applying a trained learning system.

9. The method of claim 8, wherein the trained learning system comprises a convolutional neural network (CNN).

10. The method of claim 9, wherein the CNN comprises an encoding portion, a convolutional portion, and a decoding portion.

11. The method of claim 10, wherein the encoding portion comprises four groups of layers, each group comprising two convolutional layers and a maxpool layer.

12. The method of claim 10, wherein the convolutional portion comprises two convolutional layers.

13. The method of claim 10, wherein the decoding portion comprises four groups of layers followed by a softmax layer, each group comprising a trilinear up-sampling layer, a concatenations layer, and two convolution layers.

14. The method of claim 8 wherein the trained learning system comprises an ensemble model.

15. The method of claim 14, wherein the ensemble model comprises a majority voting process used to determine a subcomponent for each voxel in the plurality of modified MRI sequences.

16. The method of claim 1, further comprising modifying the tumor segmentation.

17. The method of claim 16, further comprising recalculating one or more measurement based on the modified tumor segmentation.

18. The method of claim 16, further comprising using the modified tumor segmentation to retrain a deep learning model.

19. The method of claim 1, further comprising:
displaying a previous quantification of tumor subcomponents to a user; and
providing a comparison of a size of the tumor subcomponents.

20. A system, comprising:
a medical image database;
a computing node comprising a computer readable storage medium having program instructions embedded therewith, the program instructions executable by a processor of the computing node to cause the processor to perform a method comprising:
receiving a plurality of magnetic resonance imaging (MRI) sequences of a head of a patient, wherein each MRI sequence comprises one or more of: a T1-weighted with contrast image, a Fluid Attenuated Inversion Recovery (FLAIR) image, a T1-weighted without contrast image, a T2-weighted image, a diffusion weighted image, a diffusion tensor image, or a perfusion image;
registering each image of the plurality of MRI sequences to an anatomical atlas, wherein registering comprises:
registering the T1-weighted with contrast image or the T1-weighted without contrast image to the anatomical atlas; and
registering the FLAIR image, T2-weighted image, diffusion weighted image, diffusion tensor image, and/or perfusion image to a corresponding registered T1-weighted with contrast image or T1-weighted without contrast image;
generating a plurality of modified MRI sequences by removing a skull from each registered image in the plurality of MRI sequences;
segmenting a tumor within a brain in each image in the plurality of modified MRI sequences, wherein segmenting the tumor includes classifying one or more tumor subcomponents of the tumor based on a comparison between pixel intensities of each image in the plurality of modified MRI sequences;
quantifying the one or more tumor subcomponents; and
outputting a volumetric measurement of the one or more subcomponents.

21. A non-transitory computer readable storage medium comprising a computer program product having program instructions embodied therewith, the program instructions executable by a processor to cause the processor to perform a method comprising:

receiving a plurality of magnetic resonance imaging (MRI) sequences of a head of a patient, wherein each MRI sequence comprises one or more of: a T1-weighted with contrast image, a Fluid Attenuated Inversion Recovery (FLAIR) image, a T1-weighted without contrast image, a T2-weighted image, a diffusion weighted image, a diffusion tensor image, or a perfusion image;

registering each image of the plurality of MRI sequences to an anatomical atlas, wherein registering comprises:
registering the T1-weighted with contrast image or the T1-weighted without contrast image to the anatomical atlas; and
registering the FLAIR image, T2-weighted image, diffusion weighted image, diffusion tensor image, and/or perfusion image to a corresponding registered T1-weighted with contrast image or T1-weighted without contrast image;

generating a plurality of modified MRI sequences by removing a skull from each registered image in the plurality of MRI sequences;

segmenting a tumor within a brain in each image in the plurality of modified MRI sequences, wherein segmenting the tumor includes classifying one or more tumor subcomponents of the tumor based on a comparison between pixel intensities of each image in the plurality of modified MRI sequences;

quantifying the one or more tumor subcomponents; and outputting a volumetric measurement of the one or more subcomponents.

* * * * *